(12) United States Patent
Kennedy

(10) Patent No.: US 7,816,403 B2
(45) Date of Patent: *Oct. 19, 2010

(54) METHOD OF INHIBITING ATF/CREB AND CANCER CELL GROWTH AND PHARMACEUTICAL COMPOSITIONS FOR SAME

(75) Inventor: Thomas Preston Kennedy, Charlotte, NC (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/437,477

(22) Filed: May 14, 2003

(65) Prior Publication Data

US 2004/0019102 A1    Jan. 29, 2004

Related U.S. Application Data

(63) Continuation-in-part of application No. 09/392,122, filed on Sep. 8, 1999, now Pat. No. 6,589,987.

(51) Int. Cl.
*A61K 31/27* (2006.01)
(52) U.S. Cl. .................................... 514/483
(58) Field of Classification Search ................. 514/494, 514/599, 102, 483; 424/649
See application file for complete search history.

(56) References Cited

U.S. PATENT DOCUMENTS

| | | | |
|---|---|---|---|
| 2,454,541 A | 11/1948 | Bock et al. | |
| 4,039,669 A | 8/1977 | Beyler et al. | |
| 4,066,697 A | 1/1978 | Lawrence | |
| 4,144,272 A | 3/1979 | Bergomi et al. | |
| 4,148,885 A | 4/1979 | Renoux et al. | |
| 4,368,223 A | 1/1983 | Kobayashi et al. | |
| 4,426,372 A | 1/1984 | Borch | |
| 4,581,224 A | 4/1986 | Borch | |
| 4,594,238 A | 6/1986 | Borch | |
| 4,645,661 A | 2/1987 | Schonbaum | |
| 4,762,705 A | 8/1988 | Rubin | |
| 4,826,821 A | 5/1989 | Clements | |
| 4,870,101 A | 9/1989 | Ku et al. | |
| 4,999,347 A | 3/1991 | Sorenson | |
| 5,002,755 A | 3/1991 | Mitchell et al. | |
| 5,035,878 A | 7/1991 | Borch et al. | |
| 5,037,812 A * | 8/1991 | Berners-Price et al. | 514/105 |
| 5,166,387 A | 11/1992 | Hirschbein | |
| 5,187,193 A | 2/1993 | Borch et al. | |
| 5,206,264 A * | 4/1993 | Marangos | 514/483 |
| 5,240,914 A | 8/1993 | Rubin | |
| 5,294,430 A | 3/1994 | Borch et al. | |
| 5,373,021 A | 12/1994 | Marangos | |
| 5,380,747 A | 1/1995 | Medford et al. | |
| 5,679,777 A | 10/1997 | Anderson et al. | |
| 5,703,130 A | 12/1997 | Han et al. | |
| 5,750,351 A | 5/1998 | Medford et al. | |
| 5,759,517 A | 6/1998 | Anderson et al. | |
| 5,773,209 A | 6/1998 | Medford et al. | |
| 5,773,231 A | 6/1998 | Medford et al. | |
| 5,783,596 A | 7/1998 | Medford et al. | |
| 5,786,344 A | 7/1998 | Ratain et al. | |
| 5,792,787 A | 8/1998 | Medford et al. | |
| 5,824,664 A | 10/1998 | Schein et al. | |
| 5,827,880 A | 10/1998 | Malfroy-Camine et al. | |
| 5,877,203 A | 3/1999 | Medford et al. | |
| 5,891,633 A | 4/1999 | Gonzalez et al. | |
| 5,922,757 A | 7/1999 | Chojkier | |
| 6,057,111 A | 5/2000 | Deiss et al. | |
| 6,153,603 A * | 11/2000 | Siren | 514/102 |
| 6,156,794 A | 12/2000 | Faiman et al. | |
| 6,288,110 B1 | 9/2001 | Marikovsky | |
| 6,469,057 B1 | 10/2002 | Lai | |
| 6,548,540 B2 | 4/2003 | Kennedy | |
| 6,589,987 B2 | 7/2003 | Kennedy | |
| 6,649,591 B2 | 11/2003 | Lai | |

(Continued)

FOREIGN PATENT DOCUMENTS

CA        2384059        3/2001

(Continued)

OTHER PUBLICATIONS

Bertram et al, Environ, Carcino. & Ecotox. Revs., C11(1), 1-71, 1993.*

(Continued)

*Primary Examiner*—James D Anderson
(74) *Attorney, Agent, or Firm*—Gardner Groff Greenwald & Villanueva, PC

(57) ABSTRACT

There is provided a method for inhibiting ATF/CREB and cancer cell growth using disulfiram, administered in combination with heavy metals. It was found that disulfiram disrupts transcription factor DNA binding by forming mixed disulfides with thiols within the DNA-binding region, and that this process is facilitated by metal ions. Disulfiram administered to melanoma cells in combination with copper (II) or zinc(II) decreased expression of cyclin A, reduced proliferation in vitro, and inhibited growth of melanoma cells. The combination of oral zinc gluconate and disulfiram at currently approved doses for alcoholism stabilized tumor growth in two of three patients with Stage IV metastatic melanoma, with 12 and 17 month survivals, respectively, to date, and produced a >50% reduction in hepatic metastases in one individual.

15 Claims, 9 Drawing Sheets

U.S. PATENT DOCUMENTS

| | | | |
|---|---|---|---|
| 6,660,767 | B2 | 12/2003 | Jacobs et al. |
| 6,706,759 | B1 | 3/2004 | Kennedy |
| 6,919,425 | B2 | 7/2005 | Hong et al. |
| 6,987,127 | B2 | 1/2006 | Kennedy |
| 2002/0102604 | A1 | 8/2002 | Milne Edwards et al. |
| 2007/0232692 | A1 | 10/2007 | Kennedy |

FOREIGN PATENT DOCUMENTS

| | | |
|---|---|---|
| CA | 2424761 | 4/2002 |
| EP | 0284879 | 10/1988 |
| EP | 1214063 | 7/2005 |
| EP | 0602702 | 9/2006 |
| GB | 2 081 094 A | 2/1982 |
| GB | 2081094 | 2/1982 |
| JP | 4202139 | 7/1992 |
| JP | 4202139 A | 7/1992 |
| JP | 11-021226 | 1/1999 |
| WO | WO 91/17766 | 11/1991 |
| WO | WO 95/30415 | 11/1995 |
| WO | WO 97/05867 | 2/1997 |
| WO | WO 97/05867 A | 2/1997 |
| WO | WO 99/34763 | 7/1999 |
| WO | WO 99/34784 | 7/1999 |
| WO | WO 01/17522 | 3/2001 |
| WO | WO 01/17522 A | 3/2001 |
| WO | WO 02/28349 | 4/2002 |

OTHER PUBLICATIONS

MEDLINE AN 89350092, Craciunescu G et al, Anticancer res, May-Jun. 9, 1989, (3) 781-5, abstract.*

CANCERLIT AN 93686628, Hacker M, The toxicity of anticancer drugs, Pergamon Press, 82-105, 1991, abstract.*

Grandjean et al. Annals of Clinical and Laboratory Science, 1990, vol. 20, No. 1, pp. 28-35 (Abstract attached).*

Soliman et al. Cellular and Molecular Life Sciences, 1975, vol. 31, No. 3, pp. 280-281.*

Nobel, et al.; "Dithiocarbamates Induce Apoptosis in Thymocytes by Raising the Intracellular Level of Redox-active Copper"; *The Journal of Biological Chemistry*; vol. 270, No. 44, Nov. 3, pp. 26202-26208, 1995.

Johansson; "A review of the pharmacokinetics and pharmacodynamics of disulfiram and its metabolites"; *Acta Psychiatr Scand*, 1992: 86: pp. 15-26.

Arnelle et al.; "Diethyl Dithiocarbamate-Induced Decomposition of S-Nitrosothiols", *nitric oxide: biology and Chemistry*; February, pp. 56-64 (1997).

Verhaegh et al.; "Regulation of p53 by Metal Ions and by Antioxidants: Dithiocarbamate Down-Regulates p53 DNA-Binding Activity by Increasing the Intraclualar Level of Copper"; *Molecular and Cellular Biology*, vol. 17, No. 10, Oct. 1997, p. 5699-5706.

Schreck et al.; "Dithiocarbamates as Potent Inhibitors of Nuclear Factor κB Activation in Intact Cells"; *J. Exp. Med.*, vol. 175, May 1992, pp. 1181-1194.

Burns et al.; "1,1-Dithiolato Complexes of the Transition Elements"; *Advances in Inorganic Chemistry and Radiochemistry*, vol. 23, pp. 211-280, 1980.

*Protective Effects f Glutathione on Diethyldithiocarbamate (DDC) Cytotoxicity: A Possible Mechanism*, L. D. Trombetta et al., Toxicology and Applied Pharmacology 93, pp. 154-164, 1988.

*Inhibition of Meth-A Tumor Cell Proliferation in Combined Use of Disulfiram with Catalase*, H. Mashiba et al., Toxicology Letters, 61, pp. 75-80, 1992.

*Phase I Study of the Combination of Disulfiram with Cisplatin*, D. J. Stewart et al., Am. J. Clin. Oncol. (CCT), vol. 10, No. 6, pp. 517-519, 1987.

*Antitumour Activity of New Nitrosources on Yoshida Sarcoma Ascites Cells In Vivo*, M. Habs et al., Institute of Toxicology and Chemotherapy, German Cancer Research Center, Heidelberg, FRG, pp. 438-444, 1983.

*A Review of the Modulation of Cisplatin Toxicities by Chemoprotectants*, R. T. Dorr, Platinum and Other Metal Coordination Compounds in Cancer Chemotherapy, pp. 131-154, 1996.

*Cytotoxic Interactions of $Zn^{2+}$ In Vitro: Melanoma Cells Are More Susceptible Than Melanocytes*, J. Borovansky et al., Melanoma Research, vol. 7, pp. 449-453, 1997.

Database CAPLUS on STN (Columbus, OH) DN 136:379617, Cen D. et al., "Disulfiram induces apoptosis in human melanoma cells: a redox-related process", *Molecular Cancer Therapeutics*, 2002, 1 (3) 197-204, abstract.

Database CANCERLIT on STN (Columbus, OH) AN 83024743, Hacker M. et al., "Effect of disulfiram (tetraethylthiuram disulfide) and diethyldithiocarbamate on the bladder toxicity and antitumor activity of cyclophosphamide in mice", *Cancer Research*, Nov. 1982, 42 (11) 4490-4, abstract.

Database (DRUGU on STN (Columbus, OH) AN 2002-25463, Cen D. et al., "Redox related apoptosis of melanoma cells", *Proc. Am. Assoc. Cancer Res.*, 43, 93 Meet., 532, 2002, abstract.

Nobel C.S. et al., Mechanism of dithiocarbamate inhibition of apoptosis: thiol oxidation by dithiocarbamate disulfides directly inhibits processing of the caspase-3 proenzyme, *Chemical Research in Toxicology*, Jun. 1997, vol. 10, No. 6, pp. 636-643.

Meshnick S.R. et al., Antimalarial activity of diethyldithiocarbamate. Potentiation by Copper, *Biochemical Pharmacology*, Jul. 15, 1990, vol. 40, No. 2, pp. 213-216.

HIV infection. Dithiocarb treatment in AIDS is unsuccessful, *Fortschritte der Medizin*, Nov. 20, 1991, vol. 109, No. 33, p. 18.

Daniel, K.G., et al., Clioquinol and pyrrolidine dithiocarbamate complex with copper to form proteasome inhibitors and apoptosis inducers in human breast cancer cells, *Breast Cancer Research*, vol. 7, 2005, pp. R897-R908.

*Disulfiram and Tumor Inhibition*, H. K. A. Schirmer et al., Transactions of American Association of Genito-Urinary Surgeons, vol. 58, pp. 63-66, 1966.

Rostein et al., Carcinogenesis (London) (1988), 9(9), 1547-51.

Brar, S. Molecular Cancer Therapeutics, 2004; 3(9); pp. 1049-1060.

Lonnerdal, et al., Journal of Nutrition, 119(2): 211-214, 1989, Inhibitory effects of phytic acid and other inositol phosphates on zinc and calcium absorption in suckling rats.

Bowden et al., "Role of α4 Inegrin and VCAM-1 and CD18-Independent Neutrophil Migration Across Mouse Cardiac Endothelium," American Heart Assoc. 2002, pp. 562-569.

Meshnick et al., "Antimalarial Activity of Diethyldithiocarbamate," Biochemical Pharmacology 1990, pp. 213-216, vol. 40, No. 2.

Palazzo et al., "Myocardial ischemia-reperfusion injury in CD18- and ICAM-1-deficient mice," American Physiological Society, 1998, pp. H2300-H2307.

Vinten-Johansen, "Involvement of neutrophils in the pathogenesis of lethal myocardial reperfusion injury", European Society of Cardiology, 2003, pp. 481-497.

Khattab et al., "Copper and Zinc Levels in the Blood Serum and Urine of Bilharzial Hepatic Fibrosis", Experientia 31/3, 1975, pp. 280-281.

Polyakova et al., Determination of Calcium, Magnesium, Iron, Copper, Zinc, and Phosphorus in Blood Serum by Arc Atomic Emission Spectrometry, J. Analytical Chem, vol. 60, No. 10, 2005, pp. 937-941.

Planchon et al., "Beta-Lapachone-Induced Apoptosis in Human Prostate Cancer Cells . . . ", Experimental Cell Research, 2001, vol. 267, pp. 95-106.

Zakotnik et al., "Concomitant radiotherapy with mitomycin . . . ", Int. J. Radiation Oncology Bil. Phys., vol. 41, No. 5, pp. 1121-1127, 1998.

Asher et al., "Regulation of p53 stability and p-53-dependent apoptosis by NADH quinone oxidoreductase 1," PNAS Jan. 30, 2001, vol. 98(3), pp. 1188-1193.

Brar et al., "Reactive oxygen species from NAD(P)H:quinone oxidoreductase constitutively active NF-κB in malignant melanoma cells," Am. J. Physiol. Cell Physiol., 2001, vol. 280, pp. C659-C676.

Thornes et al., "Treatment with coumarin to prevent or delay recurrence of malignant melanoma," J. Cancer Res. Clin. Oncol., 1994, vol. 120 (suppl), pp. S32-S34.

Joseph et al., "A Unique Cytosolic Related but Distinct From NQ01 Catalyses Metabolic . . . ", British Journal of Cancer, 2000, vol. 82(7), pp. 1305-1311.

Maucher et al., "Antitumour activity of coumarin and . . . " (Rapid Communication), J. Cancer Res. Clin. Oncol., 1994, vol. 120, pp. 502-504.

Jeong-Hyung Lee et al., "Isolation and characterization of DMRT1 and its putative regulatory region in the protogyno . . . ", Cancer Chemo. Pharmacol. 1993, vol. 33, pp. 215-220.

G. Weber, "Neue systemische Therapie der Psoriasis", Hautzart, vol. 36, No. 1, 1985, pp. 20-24.

Pink et al., "NAD(P)H: QQuinone Oxidoreduvtase Activity is the Principal Determinant of . . . ", The J. of Biological Chemistry, vol. 275, No. 8, Feb. 25, 2000, pp. 5416-5424.

HIV Infection, Dithiocarb treatment in AIDS is unsuccessful, Fortschr Med. Nov. 20, 1991:109(33):18.

Hording et al., "Lack of immunomodulating effect of disulfiram on HIV positive patients," J Immunopharmac 12(2):145-147, 1990.

Habs, "Antitumour Activity of New Nitrosoureas on Yoshida Sarcoma Ascites Cells In Vivo," Institute of Toxicology and Chemotherapy, German Cancer Res. Center, Heidelberg, FRG, 1981, pp. 438-444, XP-000885514.

Lipsky et al., "In vivo inhibition of aldehyde dehydrogenase by disulfiram," Dept. of Mol. Pharmacol. and Experimental Therapeutics, Mayo Clinic/Foundation, Chemico-Biological Interactions, 130-132(1-3):93-102, 2001.

Coucouvanis, The Chemistry of the Dithioacid and 1,1-Dithiolate Complexes, 1968-1977, Department of Chemistry, University of Iowa, Iowa City, Iowa, pp. 303-469.

Clark et al., "Almost Serendipity: Alcoholism Drug Reverses Drug Resistance In Vitro," J. Natl Cancer Institute, Jun. 7, 2009, vol. 92, No. 11.

Chinery et al., "Antioxidants Reduce Cyclooxygenase-2 Expression, Prostaglandin Production, and Proliferation in Colorectal Cancer Cells," Cancer Research 58, 2323-2327, Jun. 1, 1998.

Warren and Slaga, "Mechanisms of Inhibition of Tumor Progression," Antimutagenesis and Anticarcinogenesis Mechanisms III, pp. 279-289, 1993.

Ujjani et al., "Enhancement of Cytotoxicity of Bleomycin by Dithiocarbamates: Formation of Bis(Dithiocarbamato) Cu(II)," J. Inorganic Biochemistry, 1990, 38(1), pp. 81-93.

Verhaegh et al., "Regulation of p53 by Metal Ions and by Antioxidants: Dithiocarbamate Down-Regulates p53 DNA-Binding Activity by Increasing the Intracellular Level of Copper," Molecular and Cellular Biology, Oct. 1997, pp. 5699-5706.

Arnelle et al., "Diethyl Dithiocarbamate-Induced Decomposition of S-Nitrosothiols," Nitric-Oxide: Biology and Chemistry, 1997, pp. 56-64.

Rolstein and Slaga, "Effect of exogenous glutathione on tumor progression in the murine skin multistage carcinogenesis model," Carcinogenesis, 1988, vol. 9, No. 9, pp. 1547-1551.

Hacker et al., "Effect of Disulfiram (Tetraethylthiuram Disulfide) and Diethyldithiocrbamate on the Bladder Toxicity and Antitumor Activity of Cyclophosphamide in Mice," Cancer Res. 1982, 42, 4490-4494.

Bertram and Frank, "Inhibition of chemical carcinogenesis," Environ. Carcino. & Ecolox. Revs., C11(1), 1-71 (1993).

Kroeger Smith et al., "Assault on Resistance: The Use of Computational Chemistry in the Development of Anti-HIV Drugs," Current Pharmaceutical Design, 2006, 12, 1843-1856.

Tooley et al., "Lung Function in Prematurely Delivered Rabbits Treated with a Synthetic Surfactant," Am. Rev. Respir. Dis. Sep. 1987;136(3):651-656.

Matalon et al., "Mitigation of pulmonary hyperoxic injury by administration of exogenous surfactant," J. Appl. Physiol., 62, 1987, pp. 756-761.

Loewen et al., "Alveolar hyperoxic injury in rabbits receiving exogenous surfactant," J. Appl. Physiol., 66, 1989, pp. 1087-1092.

Yang et al., "Inhibition of the DNA-binding activity of NF-kappa B by Gold Compounds In Vitro," FEBS Letters 361 (1995) pp. 89-96.

Brennan and O'Neill, "2-Mercaptoethanol restores the ability of nuclear factor kappa-B (NF kappa-B) to bind DNA in nuclear extracts from interleukin 1-treated cells incubated with pyrollidine dithiocarbamate (PDTC)," Biochem. J. (1996) 320, pp. 975-981.

Burkitt et al., "Dithiocarbamate Toxicity Toward Thymocytes Involves Their Copper-Catalyzed Conversion to Thiuram Disulfides, Which Oxidize Glutathione in a Redox Cycle Without the Release of Reactive Oxygen Species," Archives of Biochemistry and Biophysics, vol. 353, No. 1, May 1998, pp. 73-84.

Hortelano et al., "Nitric Oxide Induces Apoptosis Via Triggering Mitochondrial Permeability Transition," FEBS Letters, 410, 1997, pp. 373-377.

Reeves et al., "High Zinc Concentrations in Culture Media Affect Copper Uptake and Transport in Differentiated Human Colon Adenocarcinoma Cells (superscript-1, 2, 3)," Am Institute of Nutrition, 1996, pp. 1701-1712.

Nobel et al., "Dithiocarbamates Induce Apoptosis in Thymocytes by Raising the Intracellular Level of Redox-active Copper," J. Biological Chemistry, vol. 270, No. 44, 1995, pp. 26202-26208.

Shen et al., "Nitric oxide induces and inhibits apoptosis through different pathways," FEBS Letters 433, (1998) 125-131.

Database caplus on stn, Accession No. 1997:520740, Mateo et al., "Catalase activity in erythrocytes from colon and gastric patients," Biol. Trace Elem. Res. 1997, vol. 57(1), pp. 79-90.

Takahashi et al., Inhibition of Spontaneous Leukemia in F-344 Rats by Tetramethylthiuram Disulfide (Thiram), Gann, 74, 810-813, Dec. 1983.

Database CAPLUS on STN, accession No. 1999:4160860, Li et al., Two distinct mechanisms for inhibition of cell growth in human prostate carcinoma cells with antioxidant enzyme imbalance, abstract, Free Radical Biol. Med. 1999, vol. 22 (11/12), pp. 1554-1568.

Nielsen et al., "Effect of Tetraethylthiuramdisulphide and Diethyldithiocarbamate on Nickel Toxicokinetics in Mice," Pharmacology and Toxicology 1994, 75, 285-293.

Mashiba et al., "Inhibition of Meth-A Tumor cell proliferation in combined use of disulfiram with catalase," Toxicology Lett, 61, 1992, 75-80.

Borovansky et al., "Cytoxic interactions of Zn2+ In Vitro: Melanoma Cells are more susceptible than melanocytes," Melanoma Res 1997, 7, 449-453.

Stewart, "Phase I Study of the Combination of Disulfiram with Cisplatin," Am J Clin Oncol, 10(6):517-519, 1987.

Schirmer, Disulfiram and tumor inhibition: Transactions of the American Assoc of Genito-Urinary Surgeons, 58, 1966, 63-66, XP002108887.

Daniel et al, "Clioquinol and pyrrolidine dithiocarbamate complex with copper to form proteasome inhibitors and apoptosis inducers in human breast cancer cells," Breast Cancer Res, 7(6):R897-R908, 2005.

Habs et al., "Antitumour Activity of New Nitrosources on Yoshida Sarcoma Ascites Cells in Vivo," Inst of Toxicol and Chemotherapy, German Cancer Res Ctr, Heidelberg, FRG, 1988, 438-444.

Loo et al., "Blockage of Drug Resistance in Vitro by Disulfiram, A Drug Used to Treat Alcoholism," J of the Natl Cancer Inst., 2000, 92(11):898-902, 2000.

Nobel et al., "Disulfiram is a Potent Inhibitor of Proteases of the Caspase Family," Chem Res Toxicol, 10, pp. 1319-1324, 1997. XP002363634.

Novel et al., "Mechanism of Dithiocarbamate Inhibition of Apoptosis: Thiol Oxidation by Dithiocarbamate Disulfides Directly Inhibitions Processing of the Caspase-3 Proenzyme," Chem Res Toxicol, 1997, 10, 636-643.

Trombetta et al., "Protective Effects of Glutathione on Diethyldithiocarbamate (DDC) Cytotoxicity: A possible Mechanism," Toxicol and Applied Pharma, 93, 1988, pp. 154-164.

Habs, "Antitumour Activity of New Nitrosoureas on Yoshida Sarcoma Ascites Cells in Vivo," Inst of Toxicol and Chemotherapy, German Cancer Res Center, Heidelberg, FRG, 1981.

Tomlinson et al., "Inhibition of Human Mitochondrial Aldehyde Dehydrogenase by the Disulfiram Metabolite S-Metabolite S-Methyl=N,N-diethylthiocarbamoyl Sulfoxide," Biochem Pharmacology, 54, pp. 1253-1260, 1997.

Mays et al., "Inhibition of Human Mitochondrial Aldehyde Dehydrogenase by Metabolites of Disulfiram and Structural Characterization of the Enzyme Adduct by HPLC-Tandem Mass Spectrometry," Biochem Pharmacology, 54(11):1253-1260, 1997.

Lang et al., "Randomised, double-blind, placebo-controlled trial of dithiocarb sodium ('Imuthiol') in human immunodeficiency virus infection," Lancet, Sep. 24, 1988:2(8913):702-6.

Hersh et al., "Dithiocarb sodium (diethyldithiocarbamate) therapy in patients with symptomatic HIV infection and AIDS. A randomized, double-blind, placebo controlled, multicenter study," JAMA, Mar. 27, 1991;265(12):1538-44.

Cen et al., "Disulfiram Induces Apoptosis in Human Melanoma Cells: A Redox-Related Process," Mol Cancer Therapeutics 2002, 1, pp. 197-204.

Dtabase Cancerlit on STN, Hacker et al., accession No. 19970509, "Toxicity of Platinum Anticancer Drugs," Inst for Cell and Development Biol. 1991, pp. 82-105. Abstract.

Database Medline on STN, Craciunescu et al., accession No. 19970203, Synthesis and biological evaluation of new Rh (I) complexes with sulfonamide derivatives, Anticancer Res 1989, 9(3):781-5. Abstract Only.

Furlani et al., "Synthesis and in vitro cytostatic effect of palladium (II) and platinum (II) halide complexes with dithiocarbamic esters," Eur J Med Chem, Chim. Ther., 1986, 21(3):261-265.

Scarcia et al., "Palladium and platinum dithiocarbamato complexes containing mono- and diamines," Polyhedron 18, 1999, pp. 2827-2837.

Jain et al., "Synthesis, Spectroscopic, and Cytotoxicity Studies of Some Diamine and Diimine Platinum (II) Complexes of Diethyldithiocarbamate," J Inorganic Biochem, 1988, 33, pp. 1-9.

Mital et al., Synthesis, Characterization and Cytotoxic Studies of Diamine and Diamine Palladium(II) Complexes of Diethyldithiocarbamate and Binding of these and Analogous Platinum(II) Complexes with DNA, Inorganica Chimica Acta, 166, 1989, pp. 135-140.

Kovacic et al., "Anti-cancer action of metal complexes: electron transfer and oxidative stress?" Anti-Cancer Drug Design, 1988, 3, pp. 205-216.

Mashiba and Matdsunaga, "Augmented inhibition of MethA tumor cell proliferation in combined use of diethyldithiocarbamate with catalase or by a nondialysable fraction from co-incubation," Toxicology Lett, 1993, 66, pp. 97-104.

Dennes et al., "Studies of Zinc in Blood," 1962, J Biochem, 82, pp. 466-476.

Grandjean et al., "Trace Element Status in Alcoholism before and during Disulfiram Treatment," 1990, Annals of Clinical and Laborator Sci, 20(1):28-35. Abstract Only.

Polyakova et al., "Determination of Calcium, Magnesium, Iron, Copper, Zinc and Phosphorous in Blood Serum by Arc Atomic Emission Spectrometry," 2005, J Analytical Chemistry, 60(10):937-941.

Soliman et al., "Copper and Zing Levels in the Blood Serum and Urine of Bilharzial Hepatic Fibrosis," 1975, Cellular and Molecular Sci, 31(3):280-281.

* cited by examiner

SEQUENCE LISTING

```
<160> NUMBER OF SEQ ID NOS: 2

<210> SEQ ID NO 1
<211> LENGTH: 8
<212> TYPE: DNA
<213> ORGANISM: Artificial Sequence
<220> FEATURE:
<223> OTHER INFORMATION: cAMP response element

<400> SEQUENCE: 1
```

-continued

```
tgacgtca                                                            8

<210> SEQ ID NO 2
<211> LENGTH: 8
<212> TYPE: DNA
<213> ORGANISM: Artificial Sequence
<220> FEATURE:
<223> OTHER INFORMATION: UV-response element

<400> SEQUENCE: 2 tgacaaca                                                            8
```

# METHOD OF INHIBITING ATF/CREB AND CANCER CELL GROWTH AND PHARMACEUTICAL COMPOSITIONS FOR SAME

CROSS-REFERENCE TO RELATED APPLICATIONS

This application is a continuation-in-part of U.S. patent application Ser. No. 09/392,122, filed on Sep. 8, 1999 and now U.S. Pat. No. 6,589,987, which is incorporated herein in its entirety by reference.

BACKGROUND OF THE INVENTION

1. Field of the Invention

This invention generally relates to methods of inhibiting activating transcription factor/cAMP-responsive element-binding protein (ATF/CREB) and cancer cell growth and to pharmaceutical compositions for use in the methods. More specifically, this invention relates to methods of use and pharmaceutical compositions for treating certain cancers with a combination of a thiuram disulfide and metal ion or disulfiram chelated with a metal ion.

2. Description of the Prior Art

Cancer, the uncontrolled growth of malignant cells, is a major health problem of the modern medical era. While some malignancies, such as adenocarcinoma of the breast and lymphomas such as Hodgkin's Disease, respond relatively well to current chemotherapeutic antineoplastic drug regimens, other cancers are poorly responsive to chemotherapy, especially melanoma, non-small cell lung, pancreatic, liver, prostate and colon cancers. Even small cell cancer of the lung, initially chemotherapy sensitive, tends to return after remission, with widespread metastatic spread leading to death of the patient. Thus, better treatment approaches are needed for this illness. The biology of malignant melanomas offers an example of the importance of transcription factors for malignant cell propagation. Malignant melanomas have great propensity to metastasize and are notoriously resistant to conventional cancer treatments such as chemotherapy and γ-irradiation. Development of malignant melanoma in humans progresses through a multistage process, with transition from melanocyte to nevi, to radial growth, and subsequently to the vertical growth, metastatic phenotype of autonomous melanomas, associated with decreased dependence on growth factors, diminished anchorage dependence, reduced contact inhibition and increased radiation and drug resistance.

Much of the molecular understanding of melanoma progression has come from studying the response of cultured melanoma cells to mitogenic stimuli. In culture, melanocyte proliferation and differentiation are positively regulated by agents that increase cAMP (Cox, et al., *Nucleic Acids Res.* 20:4881-4887 (1992); Halaban, et al., *J. Cell Biol.* 97:480-488 (1983); Jean, et al., *J. Biol. Chem.* 273:24884-24890 (1998); Klatt, et al., *J. Biol. Chem.* 274:15857-15864 (1999); Lehmann, et. al., *Proc. Natl. Acad. Sci. U.S.A.* 89:9891-9895 (1989); Luca, et al., *Melanoma Res.* 3:35-41(1993); Richards, et al., *J. Biol. Chem.* 271:13716-13723 (1996); and Xie, et al., *Oncogene* 15:2069-2075 (1997)), and several cAMP responsive transcription factors binding to CRE (the consensus motif 5'-TGACGTCA-3', or cAMP response element) play prominent roles in mediating melanoma growth and metastasis. In MeWo melanoma cells, the transcription factor CREB (for CRE-binding protein) and its associated family member ATF-1 promote tumor growth, metastases and survival through CRE-dependent gene expression. Jean, et al., supra. Expression of the dominant negative KCREB construct in metastatic MeWo melanoma cells decreases their tumorigenicity and metastatic potential in nude mice. Xie, et al., *Cancer Res.* 57:2295-2303 (1997). The KCREB-transfected cells display a significant decrease in matrix metalloproteinase 2 (MPP2, the 72 kDa collagenase type IV) mRNA and activity, resulting in decreased invasiveness through the basement membrane, an important component of metastatic potential.

The cell surface adhesion molecule MCAM/MUC18, which is involved in metastasis of melanoma is also down-regulated by KCREB transfection. Xie, et al., *Cancer Res.*, supra. In addition, expression of KCREB in MeWo cells renders them susceptible to thapsigargin-induced apoptosis, suggesting that CREB and its associated proteins act as survival factors for human melanoma cells, thereby contributing to the acquisition of the malignant phenotype. Jean, et al., supra.

Melanoma cells aberrantly express the major histocompatibility complex class II (MHC II) antigens normally found only in B-lymphocytes and antigen presenting cells of the monocyte/macrophage cell line. Cox, et al., *Nucleic Acids Res.* 20:4881-4887 (1992). In $B_{16}$ melanoma cells this is due to activation of the MHC II DRα promoter by constitutive activation of an ATF/CREB motif. CREB family proteins also bind to the UV-response element (URE, 5'-TGACAACA-3'), and URE binding of the CREB family member ATF-2 confers resistance to irradiation and to the chemotherapeutic drugs cis-platinum, 1-β-D-arabinofuranosylcytosine (araC) or mitomycin C in MeWo melanoma lines. Ronai, et al., *Oncogene* 16:523-531 (1998). Thus, CREB family transcription factors play important roles in the malignant potential of this tumor type. Thus, targeted molecular disruption of ATF/CREB-mediated transcription might be therapeutically useful for controlling growth and metastases of relatively treatment-resistant malignant melanoma. Jean, supra, and Ronai, supra.

Transcription factors would seem particularly sensitive to this approach. The positively charged DNA binding domain of many transcription factors contains cysteines that can be oxidatively modified by agents such as hydrogen peroxide or nitric oxide (NO*), stimulating repair processes that result in formation of mixed disulfides between glutathione (GSH) and protein thiols. As a consequence of this so-called protein "S-glutathionylation", the usually positively charged transcription factor DNA binding domain develops an electronegative charge imparted by dual carboxylate end groups of GSH. The change in charge disrupts transcription factor binding to its respective DNA consensus sequence. Sies, *Free Rad. Biol. Med.* 27:916-921 (1999); Klatt, et al., supra. This mechanism explains how NO* inhibits c-Jun DNA binding by specifically targeted S-glutathionylation of cysteines within the DNA binding region, and a similar mechanism has been suggested for how nitrosative stress functionally inhibits the activity of Fos, ATF/CREB, Myb and Rel/NF-κB family transcription factors. See, Klatt, et al., supra. The transcription factors nuclear factor-κB (NF-κB), activator protein-1 (AP-1) and ATF/CREB all contain cysteines in their DNA binding regions as reactive sites for mixed disulfide formation. Klatt, et al., supra; Pineda-Molina, et al., *Biochem.* 40:14134-14142 (2001); Marshall, et al., *Biochem.* 40:1688-1693 (2001); Nikitovic, et al., *Biochem. Biophys. Res. Commun.* 242:109-112 (1998); Goren, et al., *J. Mol. Biol.* 313:695-709 (2001); Richards, et al., *J. Biol. Chem.* 271:13716-13723 (1996).

One therapeutic use for this approach is treatment of malignant melanoma. Melanomas are dependent for growth and metastasis on activation of distinct transcription factors, such as NF-κB (Yang, et al., *Cancer Res.* 61:4901-4909(2001)), and ATF/CREB transcription factors binding to the cyclic AMP response element CRE (Xie, et al., *Oncogene,* supra); Jean, et al., supra; Xie, et al., *Cancer Res.,* supra; Cox, et al., *Nucleic Acids Res.* 20:4881-4887 (1992); Ronai, et al., *Oncogene* 16:523-531 (1999)). Targeted molecular disruption of ATF/CREB-mediated transcription has been proposed as a strategy to control melanoma growth and metastasis (Jean, et al., supra; Ronai, et al., supra).

The dithiocarbamate disulfide, disulfiram, was once used as a treatment for alcoholism, but has been reported to reverse in vitro resistance of human tumors to chemotherapy drugs by blocking maturation of the P-glycoprotein membrane pump that extrudes chemotherapeutic agents from the cell. Loo, et al., *J. Natl. Cancer Inst.* 92:898-902 (2000). Disulfiram also enhances efficacy of 5-fluorouracil against human colorectal cancer cell lines (Wang, et al., *Cancer Res.* 43:954 (abstract) (2002)), inhibits DNA topoisomerases (Yakisch, et al., *Biochem. Biphys. Res. Commun.* 289:586-590 (2002)), induces apoptosis in cultured melanoma cells (Cen, et al., *Mol. Cancer Therapeut.* 1:197-204 (2002)), and reduces angiogenesis and inhibits growth of C6 glioma and metastases of Lewis lung carcinoma in mice (Marikovsky, et al., *Int. J Cancer* 97:34-41 (2002)).

Dithiocarbamates comprise a broad class of compounds possessing a RR'NC(S)SR" functional groups, having the ability to complex metals (Nobel, et al., *J. Biol. Chem.* 270: 26202-26208 (1995)) and react with sulfhydryl groups (Orrenius, et al., *Biochem. Soc. Trans.* 24:1032-1038 (1996)) and glutathione (Burkitt, et al., *Arch. Biochem. Biophys.* 353:73-84 (1998)). After oxidation by copper ions to their corresponding disulfides, dithiocarbamates inhibit critical sulfhydryls in proteins such as cysteine proteases by forming mixed disulfides with thiols (Nobel, et al., *Chem. Res. Toxicol.* 10:636-643 (1997)).

It is therefore an object of the present invention to provide a method for the inhibition of ATF/CREB growth to treat certain cancers.

Another object of the present invention is to provide a method for treating certain cancers by administering to a patient a therapeutically effective amount of a thiuram disulfide and a heavy metal ion.

Yet another object of the present invention is to provide pharmaceutical compositions for the treatment of cancer.

It is still another object of the present invention to provide a relatively less toxic agent available for use alone or in combination with current drugs in order to better treat cancer patients without risking injury from the therapy itself.

BRIEF SUMMARY OF THE INVENTION

Occasionally, in the search for novel therapies, a new use is found for an old drug. It was found that disulfiram administered in combination with metal ions provides a pharmacologic approach to inhibiting cellular proliferation of tumors by forming mixed disulfides that disrupt protein function. Thus, the present invention provides a method of inhibiting ATF/CREB and melanoma growth, thereby treating established cancer using disulfiram in combination with a heavy metal ion. It has been discovered that the antiproliferative and antineoplastic effect of disulfiram on established tumor cells is heavy metal ion-dependent. Further, the tumor cell growth inhibition effect of disulfiram can be significantly enhanced by the addition of heavy metal ions. Suitable heavy metal ions include but are not limited to ions of arsenic, bismuth, cobalt, copper, chromium, gallium, gold, iron, manganese, nickel, silver, titanium, vanadium, selenium, and zinc, which can induce an acute phase response in the tumor cells.

Accordingly, this invention provides a method for treating established cancer in a patient comprising administering to the patient a therapeutically effective amount of a dithiocarbamate disulfide, or thiuram disulfide, preferably disulfiram, and a heavy metal ion. In a preferred embodiment, the heavy metal ion is administered as a complex or chelate with the thiuram disulfide. In another preferred embodiment, the thiuram disulfide and the heavy metal ion are administered in combination with another anti cancer agent.

In addition, the present invention provides a pharmaceutical composition which comprises a pharmaceutically acceptable carrier, and a complex between a thiuram disulfide and a heavy metal ion. Optionally, the composition can further contain another anticancer agent. The active compounds of this invention can be administered through a variety of administration routes. For example, they can be administered orally, intravenously, indermally, subcutaneously and topically.

The present invention is effective for treating cancers including, but not limited to, melanoma, non-small cell lung cancer, small cell lung cancer, renal cancer, colorectal cancer, breast cancer, pancreatic cancer, gastric cancer, bladder cancer, ovarian cancer, uterine cancer, lymphoma, and prostate cancer. In particular, the present invention will be especially effective in treating melanoma, lung cancer, breast cancer, and prostate carcinoma.

BRIEF DESCRIPTION OF THE DRAWINGS

Figure 1:
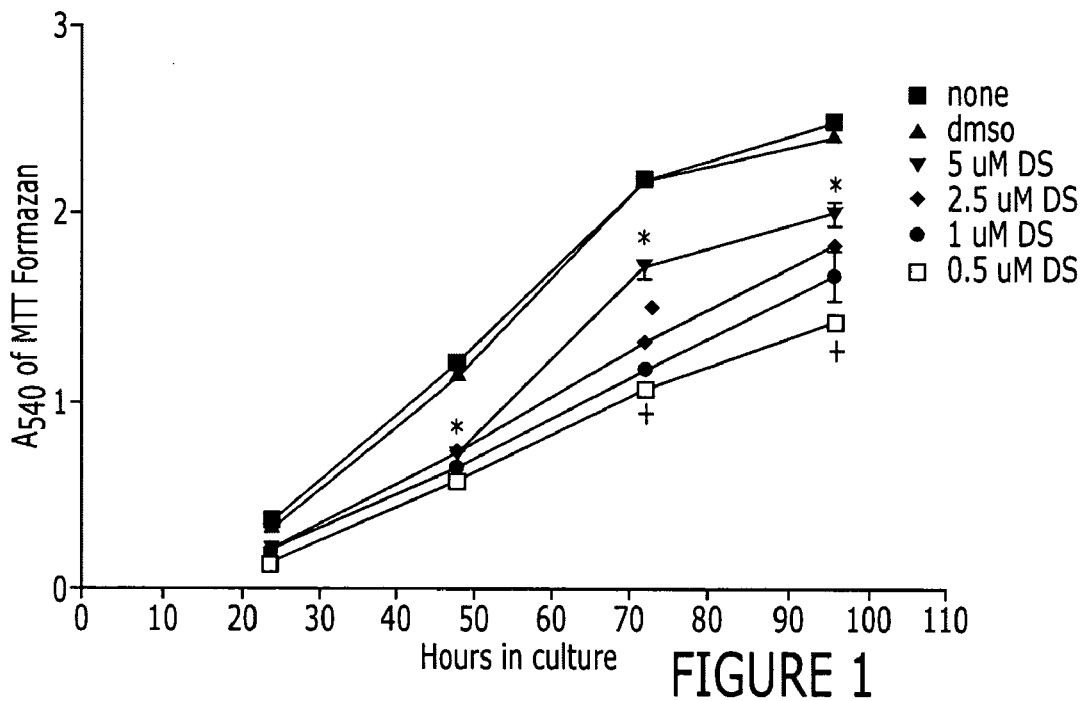
Figure 2:
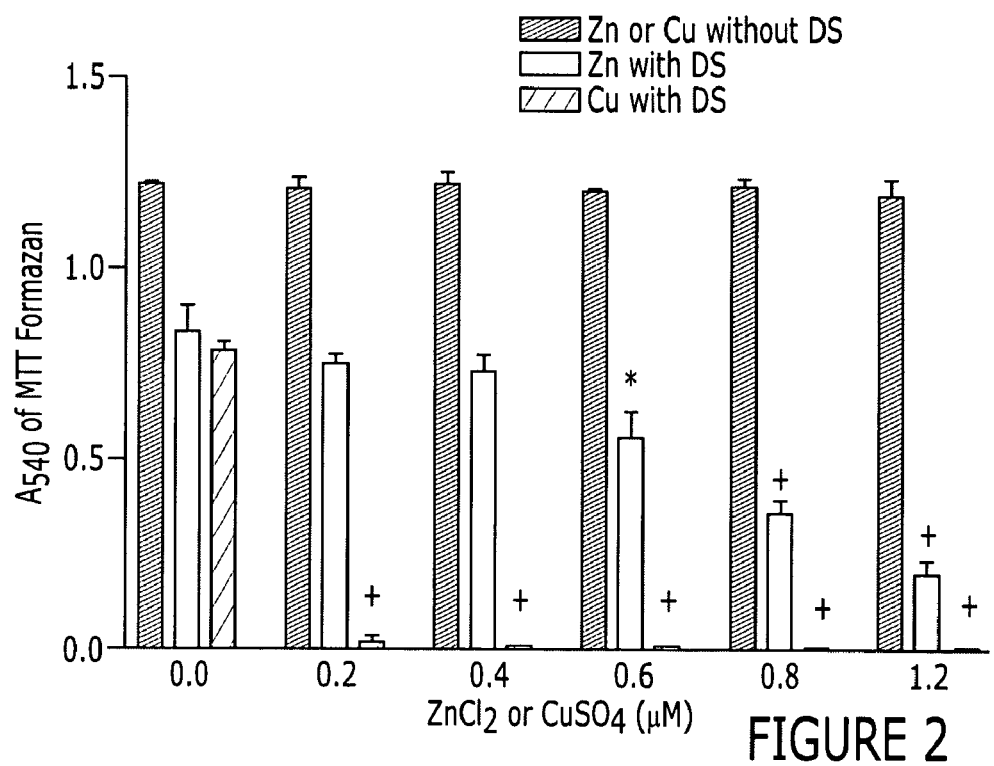
Figure 3:
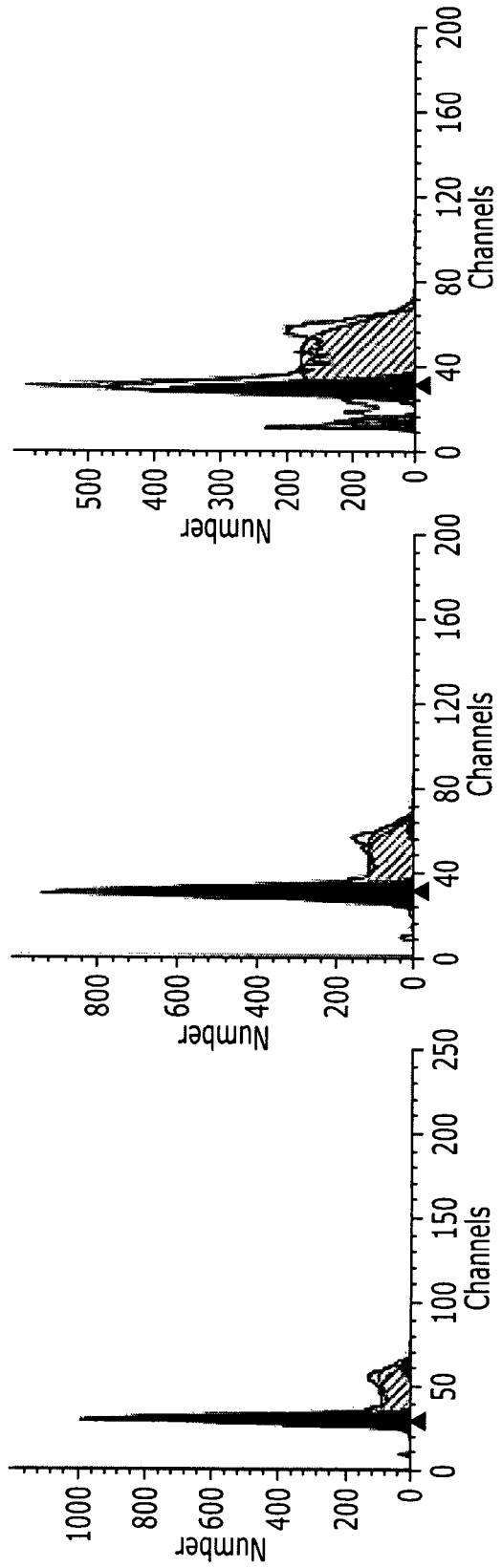
Figure 4:
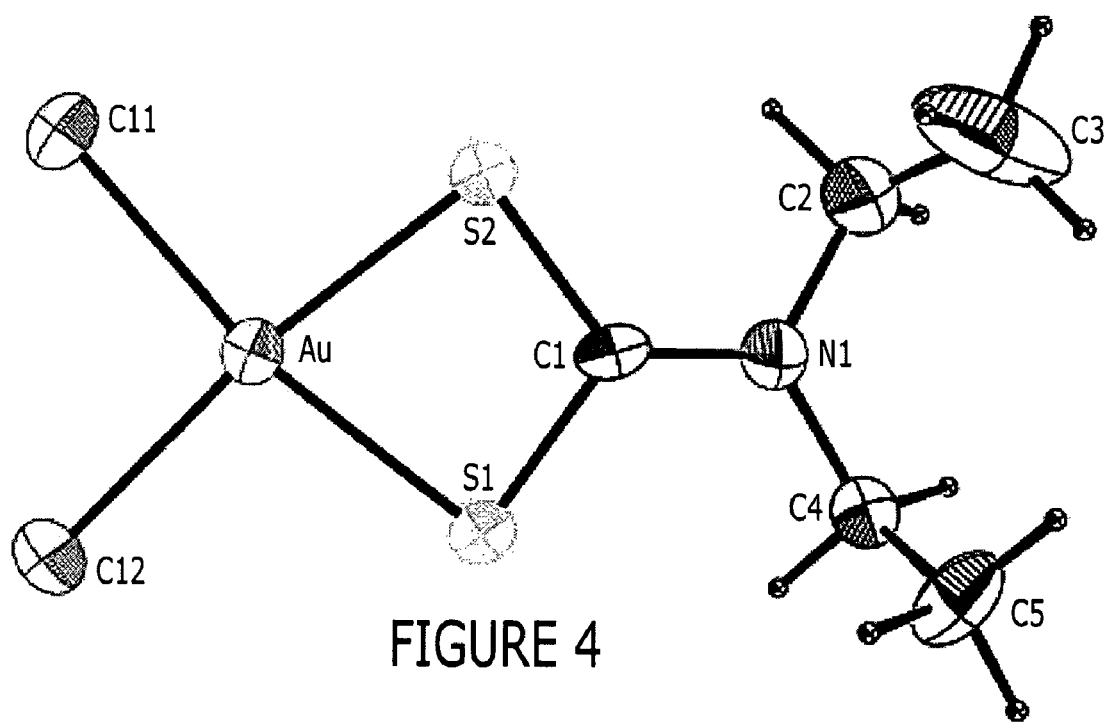
Figure 5B:
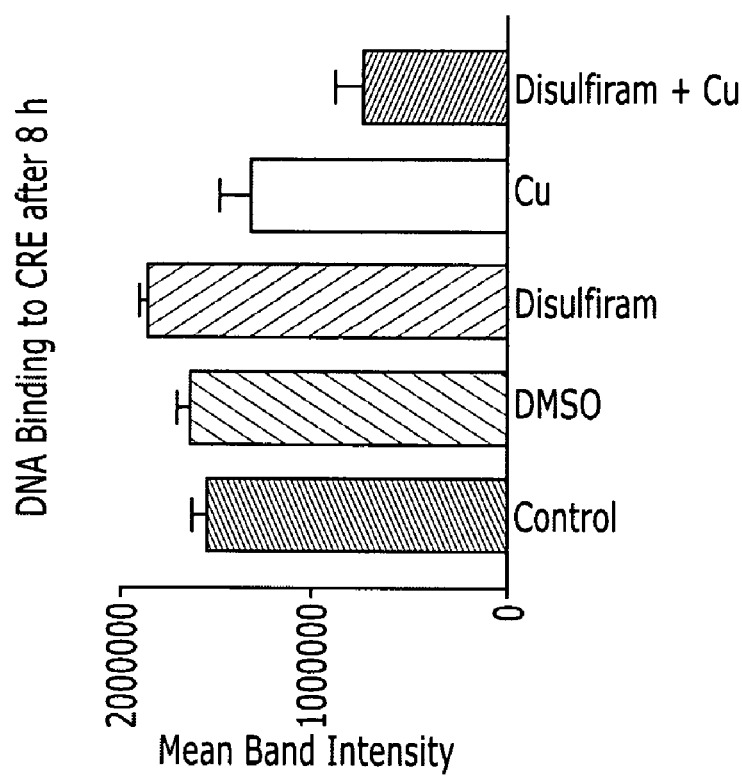
Figure 5A:
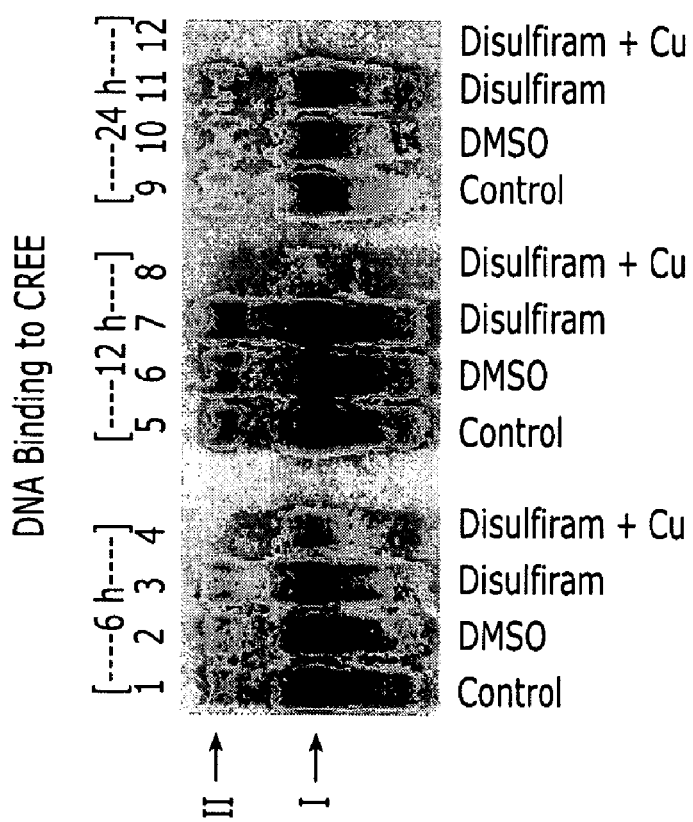
Figures 5C, 5D:
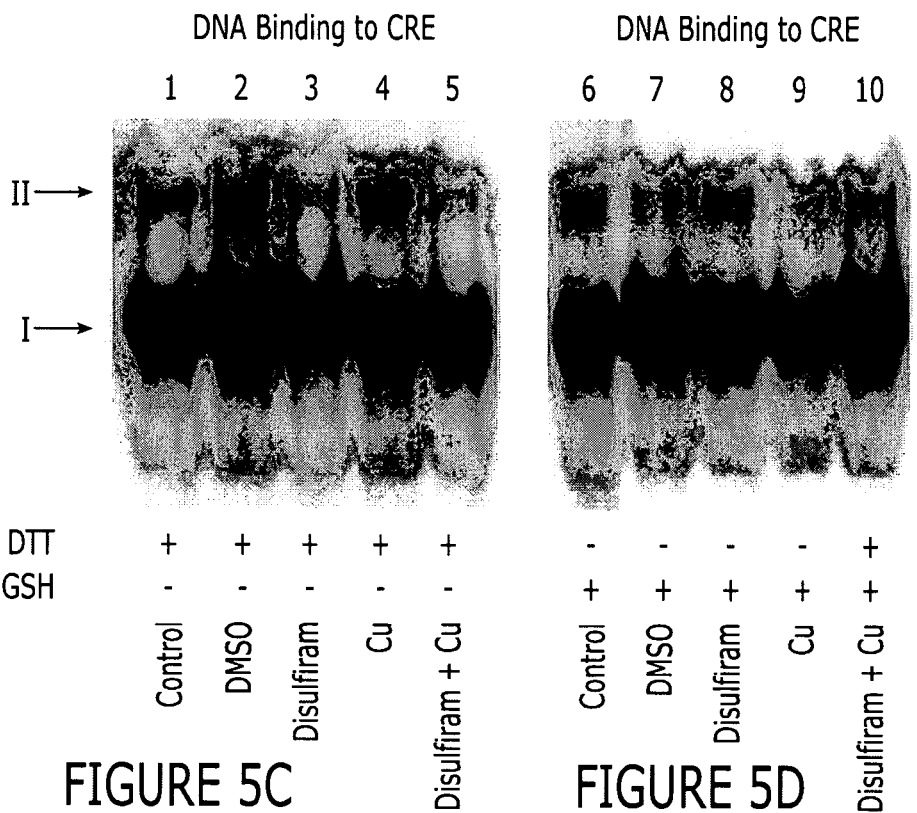
Figures 6A, 6B:
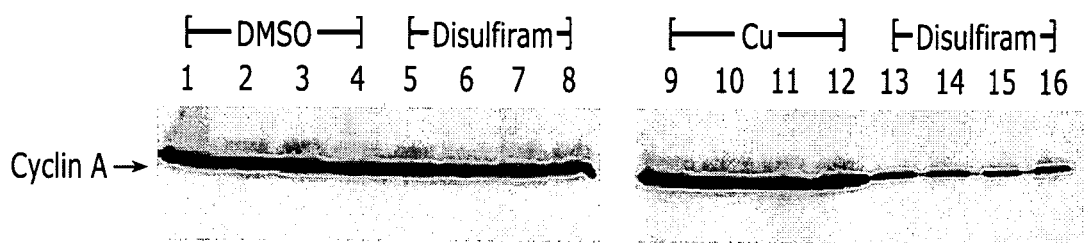
Figure 6C:
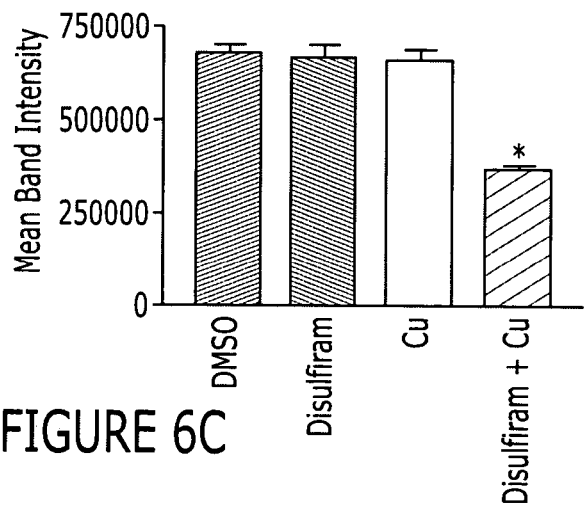
Figure 7:
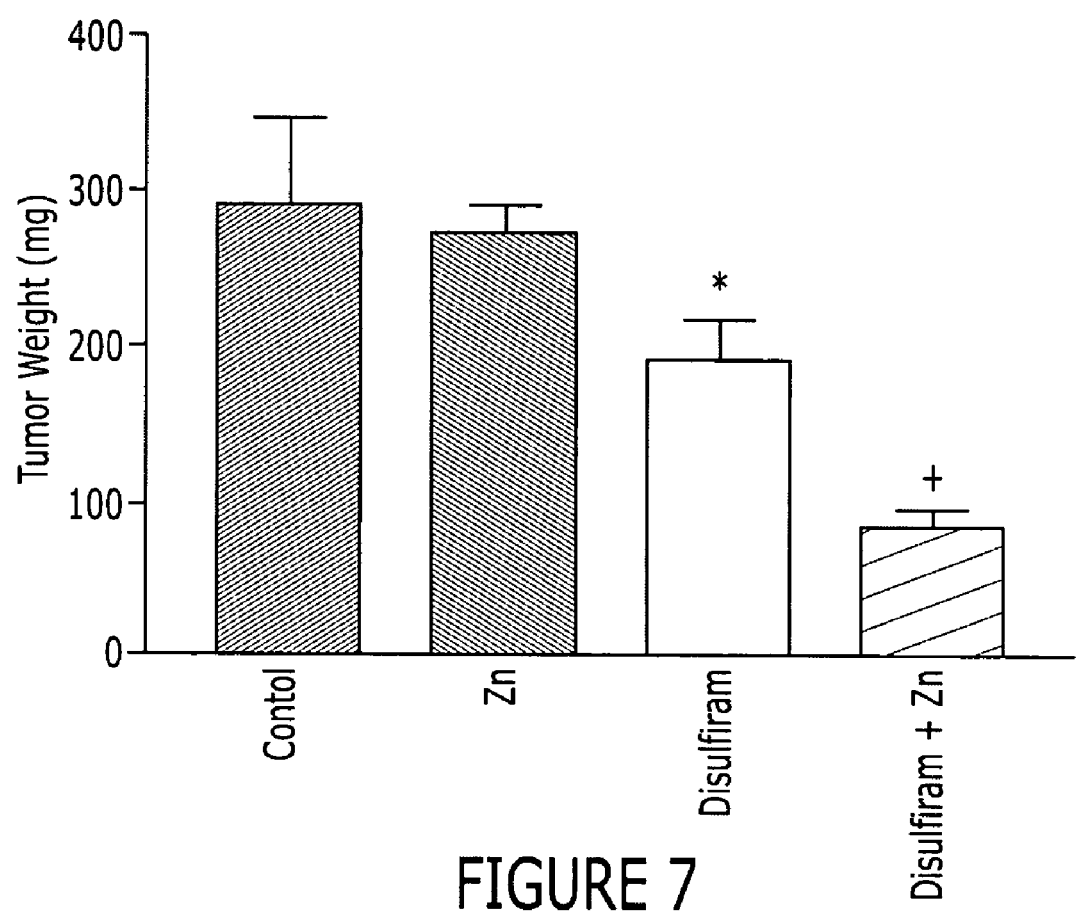
Figures 8A, 8B, 8C, 8D, 8E, 8F:
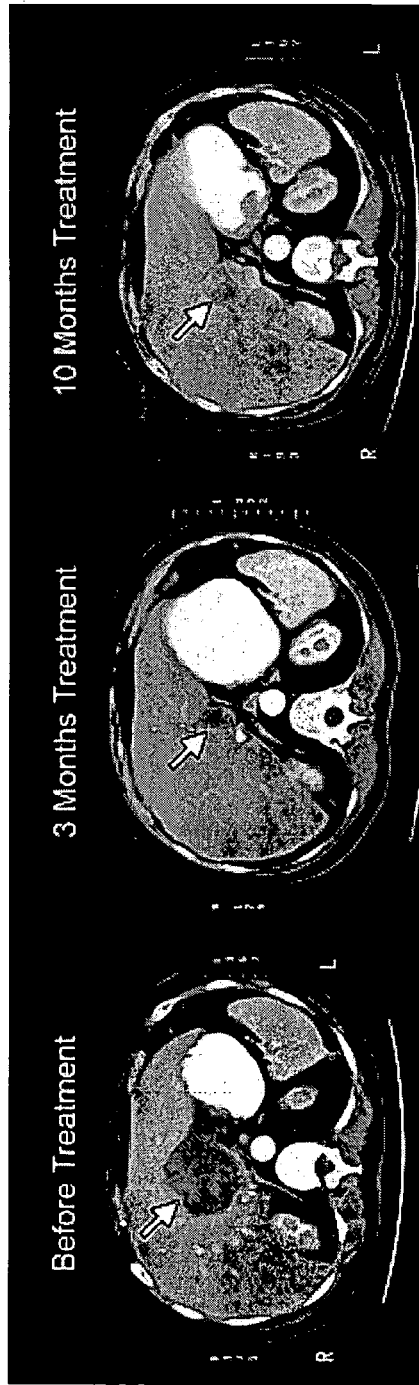
Figure 9:
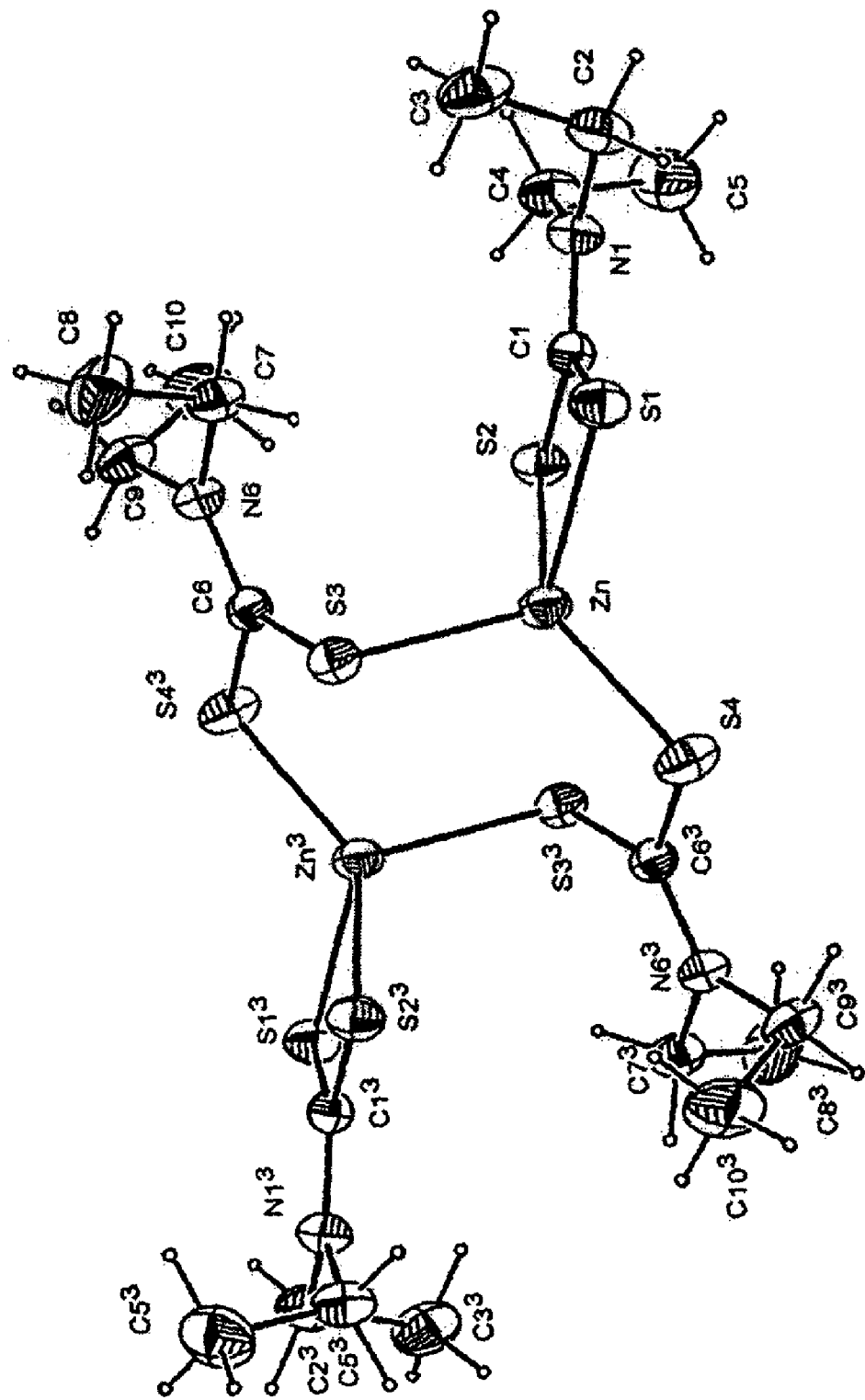
Figures 9A, 9B:
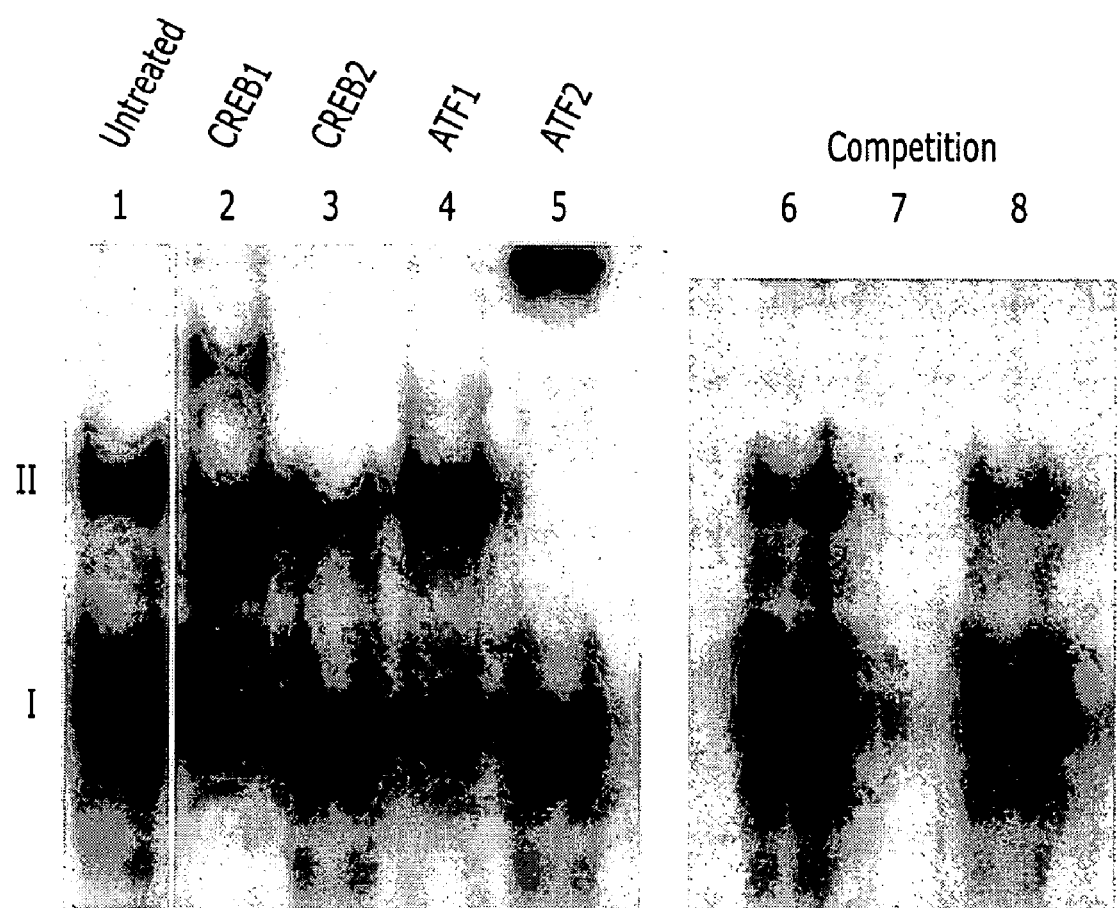

Having thus described the invention in general terms, reference will now be made to the accompanying drawings, which are not necessarily drawn to scale, and wherein:

FIG. 1 shows that disulfiram inhibits proliferation of CRL1619 human melanoma cells;

FIG. 2 shows that the supplementation of growth medium with copper(II) or zinc(II) enhances the antiproliferative activity of disulfiram;

FIG. 3A shows unsynchronized CRL 1619 melanoma cells grown in the presence of DMSO;

FIG. 3B shows that unsynchronized CRL 1619 melanoma cells grown in the presence of disulfiram;

FIG. 3C shows unsynchronized CRL 1619 melanoma cells grown in the presence of disulfiram combined with copper(II) induces S-phase cell cycle arrest and apoptosis;

FIG. 4 shows X-Ray crystallographic structure of gold(III) diethyldithiocarbamate;

FIGS. 5A and 5B show that disulfiram and metals inhibit transcription factor binding to the cyclic AMP response element;

FIG. 5C shows treatment of melanoma cells with disulfiram and copper (II) inhibits transcription factor binding to CRE;

FIG. 5D shows the inhibitory effects of disulfiram or disulfiram plus copper(II) on transcription factor binding are potentiated in the presence of glutathione (GSH);

FIG. 6 shows that disulfiram and copper(II) reduce expression of the cell-cycle protein cyclin A;

FIG. 7 shows that disulfiram plus zinc supplementation decreases malignant melanoma growth in mice;

FIG. 8 shows that disulfiram and zinc gluconate reduce hepatic tumor volume in a patient with metastatic ocular melanoma; and FIG. 9 shows X-Ray crystallographic structure of zinc(II) diethyldithiocarbamate.

DETAILED DESCRIPTION OF THE INVENTION

The present invention now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements.

Disulfiram blocks ATF/CREB, reduces cyclin A expression, cell cycle progression into $G_2$-M and melanoma proliferation in vitro in a manner facilitated by heavy metal ions. It has been found that enhancement of these effects in the presence of both disulfiram and heavy metal ions provides specific biochemical events not readily produced by disulfiram alone.

As used herein, the term "thiuram disulfides" refers to compounds having the formula of:

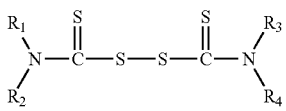

where $R_1$, $R_2$, $R_3$, and $R_4$ are the same or different and represents hydrogen, and unsubstituted or substituted alkyl, alkenyl, alkynyl, aryl and alkoxy or a heterocycle containing nitrogen, oxygen, or sulfur and from 5-8 carbon atoms. Preferably, $R_1$, $R_2$, $R_3$, and $R_4$ taken separately are saturated aliphatic radicals having 1 to 6 carbon atoms such as methyl, ethyl, n-propyl, i-propyl, n-butyl, i-butyl, n-pentyl, i-pentyl, n-hexyl, neohexyl, i-hexyl, cyclohexyl methyl, beta-cyclopentylethyl, nitro, lower alkyl-nitro, or halo-substituted phenyl, lower alkyl- or halo-substituted benzyl, or lower alkyl-nitro, or halo-substituted, phenylethyl, morpholinyl, thiomorpholinyl piperidinyl, piperazinyl and the like. Most preferably, $R_1$, $R_2$, $R_3$, and $R_4$, taken separately, are methyl, ethyl or isopropyl. Typically, $R_1$ and $R_2$ are not both hydrogen, and $R_3$, and $R_4$ are not both hydrogen. It is noted that the alkyl groups can include cycloalkyl and heterocycloalkyl groups. $R_1$, $R_2$, and the N atom in the formula can together form an N-heterocyclic ring, which is, e.g., heterocycloalkyl or heterocycloaryl. Likewise, $R_3$, $R_4$ and the N atom in the formula can together an N-heterocyclic ring, which is, e.g., heterocycloalkyl or heterocycloaryl. Thus, a thiuram disulfide is the disulfide form of dithiocarbamates which have a reduced sulfhydryl group. Many thiocarbamates are known and synthesized in the art. Nonlimiting examples of dithiocarbamates include diethyldithiocarbamate, pyrrolidinedithiocarbamate, N-methyl, N-ethyldithiocarbamates, hexamethylenedithiocarbamate, imadazolinedithiocarbamates, dibenzyldithiocarbamate, dimethylenedithiocarbamate, dipropyldithiocarbamate, dibutyldithiocarbamate, diamyldithiocarbamate, N-methyl, N-cyclopropylmethyldithiocarbamate, cyclohexylamyldithiocarbamate, pentamethylenedithiocarbamate, dihydroxyethyldithiocarbamate, N-methylglucosamine dithiocarbamate, and salts and derivatives thereof Typically, a sulfhydryl-containing dithiocarbamate can be oxidized to form a thiuram disulfide.

Any pharmaceutically acceptable form of thiuram disulfides as defined above can be used. For example, tetraalkylthiuram disulfide, preferably tetraethylthiuram disulfide, known as disulfiram, is used in the method of this invention. Disulfiram has the following formula:

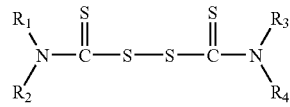

where $R_1$, $R_2$, $R_3$, and $R_4$ are all ethyl. Disulfiram has been used clinically in the treatment of alcohol abuse, in which disulfiram inhibits hepatic aldehyde dehydrogenase. Methods of making thiuram disulfides are generally known in the art. Exemplary methods are disclosed in, e.g., Thorn, et al., *The Dithiocarbamates and Related Compounds,* Elsevier, N.Y., 1962; and U.S. Pat. Nos. 5,166,387, 4,144,272, 4,066,697, 1,782,111, and 1,796,977, all of which are incorporated herein by reference.

This invention provides a method for treating cancer in a patient. The term "treating cancer" as used herein, specifically refers to administering therapeutic agents to a patient diagnosed of cancer, i.e., having established cancer in the patient, to inhibit the further growth or spread of the malignant cells in the cancerous tissue, and/or to cause the death of the malignant cells. In accordance with the present invention, it has been discovered that thiuram disulfides, such as disulfiram, can inhibit the growth of tumor cells in a heavy metal ion-dependent manner. Specifically, heavy metal ions such as copper, zinc, gold, and silver ions significantly enhance the inhibitory effect of thiuram disulfides on tumor cells, while the depletion of such heavy metal ions prevents growth inhibition by disulfiram.

Accordingly, in accordance with one aspect of this invention, a method for treating an established cancer in a patient is provided. A thiuram disulfide and a heavy metal ion can be administered to a patient having established cancer to treat the cancer. Preferably, the thiuram disulfide is a tetra alkyl thiuram disulfide such as tetraethylthiuram disulfide, i.e., disulfiram.

Non-limiting examples of heavy metal ions include ions of arsenic, bismuth, cobalt, copper, chromium, gallium, gold, iron, manganese, nickel, silver, titanium, vanadium, selenium and zinc. Preferably, zinc, gold, silver, gallium and copper ions are used. One or more thiuram disulfide compounds and one or more heavy metal ions can be administered to a patient. Sources of such heavy metal ions are known to those skilled in the art. For example, such ions can be provided in a sulfate salt, or chloride salt form, or any other pharmaceutically suitable forms. The thiuram disulfide compound and the heavy metal ion can be administered in combination or separately. For example, disulfiram and zinc gluconate may be given separately. However, the disulfiram and metal ion can also be administered as a chelate. As is known in the art, thiuram disulfide compounds are excellent chelating agents and can chelate heavy metal ions to form chelates. Preparation of chelates of thiuram disulfide compounds and heavy metal ions are known to those skilled in the art. For example, chelates of disulfiram and copper, zinc, silver, or gold ions can be conveniently synthesized by mixing, in a suitable solvents, disulfiram with, e.g., $CuSO_4$, $ZnCl_2$, $C_3H_5AgO_3$, or $HAuCl_4 3H_2O$ to allow chelates to be formed. X-ray crystallographic structures of chelates of disulfiram/gold and disulfiram/zinc are shown in FIG. 4 and FIG. 9, respectively. Other thiuram disulfide compound-heavy metal ion chelates are disclosed in, e.g., Burns, et al., *Adv. Inorg. Chem. Radiochem.* 23:211-280 (1980), which is incorporated herein by reference.

In accordance with another aspect of this invention, the method of this invention can be used in combination with a conventional anticancer therapy. For example, the method of this invention can be complemented by a conventional radiation therapy or chemotherapy. Thus, in one embodiment of this invention, the method of this invention comprises administering to a patient a thiuram disulfide/metal ion compound and an anticancer agent. Any anticancer agents known in the art can be used in this invention so long as it is pharmaceutically compatible with the thiuram disulfide compounds and heavy metal ions used. By "pharmaceutically compatible" it is intended that the other anticancer agent will not interact or react with the above composition, directly or indirectly, in such a way as to adversely affect the effect of the treatment of cancer, or to cause any significant adverse side reaction in the patient.

Exemplary anticancer agents known in the art include cisplatin, carmustine, herceptin, carboplatin, cyclophosphamide, nitrosoureas, fotemustine, vindesine, etoposide, daunorubicin, adriamycin, paclitaxel, taxotere, fluorouracil, methotrexate, melphalan, bleomycin, salicylates, aspirin, piroxicam, ibuprofen, indomethacin, naprosyn, diclofenac, tolmetin, ketoprofen, nabumetone, oxaprozin, doxirubicin, nonselective cyclooxygenase inhibitors such as nonsteroidal anti-inflammatory agents (NSAIDS), and selective cyclooxygenase-2 (COX-2) inhibitors.

The anticancer agent used can be administered simultaneously in the same pharmaceutical preparation with the thiuram disulfide compound and heavy metal ions or the disulfiram/metal ion complex. The anticancer agent can also be administered at about same time but by a separate administration. Alternatively, the anticancer agent can be administered at a different time from the administration of the thiuram disulfide compound, heavy metal ions, or ceruloplasmin. Some minor degree of experimentation may be required to determine the best manner of administration, this being well within the capability of one skilled in the art once apprised of the present disclosure.

The methods of this invention are suitable for inhibiting ATF/CREB and melanoma growth. Thus, the methods are useful for treating cancers in animals, especially mammals such as canine, bovine, porcine, and other animals. Advantageously, the methods are used in treating human patients. The methods are useful for treating various types of cancer, including but not limited to melanoma, non-small cell lung cancer, small cell lung cancer, renal cancer, colorectal cancer, breast cancer, pancreatic cancer, gastric cancer, bladder cancer, liver cancer, ovarian cancer, uterine cancer, lymphoma, and prostate cancer. In particular, the present invention will be effective in treating melanoma, lung cancer, breast cancer, and prostate carcinoma.

Disulfiram has been used clinically in treating alcohol abuse. A dosage form of disulfiram approved by the U.S. Food and Drug Administration (Antabuse®) can be purchased in 250 and 500 mg tablets for oral administration from Wyeth-Ayerst Laboratories (P.O. Box 8299, Philadelphia, Pa 19101). The pharmacology and toxicology of Antabuse® are detailed in Physicians Desk Reference, 50th edition, Medical Economics, Montvale, N.J., pages 2695-2696. Steady-state serum levels of approximately 1.3 μM have been measured in humans taking repeated doses of 250 mg disulfiram daily. See, e.g., Faiman et al., *Clin. Pharmacol. Ther.* 36:520-526 (1984); and Johansson, *Acta Psychiatr. Scand., Suppl.* 369: 15-26 (1992). Disulfiram is relatively non-toxic, with an $LD_{50}$ in rodents of 8.6 g/kg. See, e.g., *The Merck Index,* 10th Edition, Reference 3382, Merck & Co., Rahway, N.J., 1983, page 491. Disulfiram can be used in a similar dosage in the present invention. The therapeutically effective amount for other thiuram disulfide compounds may also be estimated or calculated based on the above dosage ranges of disulfiram and the molecular weights of disulfiram and the other thiuram disulfide compounds, or by other methods known in the art.

The active compounds of this invention are typically administered in a pharmaceutically acceptable carrier through any appropriate routes such as parenteral, intravenous, oral, intradermal, subcutaneous, or topical administration. The active compounds of this invention are administered at a therapeutically effective amount to achieve the desired therapeutic effect without causing any serious adverse effects in the patient treated.

Heavy metal ions can be administered separately as an aqueous solution or oral form in a pharmaceutically suitable salt form. However, they can also be administered in a chelate form in which the ions are complexed with thiuram disulfide compounds. Thus, the amount of heavy metal ions to be used advantageously is proportional to the amount of thiuram disulfide compound to be administered based on the molar ratio between a heavy metal ion and thiuram disulfide compound in the chelate. Methods for preparing such chelates or complexes are known and the preferred methods are disclosed above and in the examples below.

Advantageously, the active compounds are delivered to the patient parenterally, i.e., intravenously or intramuscularly. For parenteral administration, the active compounds can be formulated into solutions or suspensions, or in lyophilized forms for conversion into solutions or suspensions before use. Sterile water, physiological saline, e.g., phosphate buffered saline (PBS) can be used conveniently as the pharmaceutically acceptable carriers or diluents. Conventional solvents, surfactants, stabilizers, pH balancing buffers, anti-bacteria agents, and antioxidants can all be used in the parenteral formulations, including but not limited to acetates, citrates or phosphates buffers, sodium chloride, dextrose, fixed oils, glycerine, polyethylene glycol, propylene glycol, benzyl alcohol, methyl parabens, ascorbic acid, sodium bisulfite, and the like. The parenteral formulation can be stored in any conventional containers such as vials, ampoules, and syringes.

The active compounds can also be delivered orally in enclosed gelatin capsules or compressed tablets. Capsules and tablets can be prepared in any conventional techniques. For example, the active compounds can be incorporated into a formulation which includes pharmaceutically acceptable carriers such as excipients (e.g., starch, lactose), binders (e.g., gelatin, cellulose, gum tragacanth), disintegrating agents (e.g., alginate, Primogel, and corn starch), lubricants (e.g., magnesium stearate, silicon dioxide), and sweetening or flavoring agents (e.g., glucose, sucrose, saccharin, methyl salicylate, and peppermint). Various coatings can also be prepared for the capsules and tablets to modify the flavors, tastes, colors, and shapes of the capsules and tablets. In addition, liquid carriers such as fatty oil can also be included in capsules.

Other forms of oral formulations such as chewing gum, suspension, syrup, wafer, elixir, and the like can also be prepared containing the active compounds used in this invention. Various modifying agents for flavors, tastes, colors, and shapes of the special forms can also be included. In addition, for convenient administration by enteral feeding tube in patients unable to swallow, the active compounds can be dissolved in an acceptable lipophilic vegetable oil vehicle such as olive oil, corn oil and safflower oil.

The active compounds can also be administered topically through rectal, vaginal, nasal or mucosal applications. Topical formulations are generally known in the art including creams, gels, ointments, lotions, powders, pastes, suspensions, sprays, and aerosols. Typically, topical formulations include one or more thickening agents, humectants, and/or emollients including but not limited to xanthan gum, petrolatum, beeswax, or polyethylene glycol, sorbitol, mineral oil, lanolin, squalene, and the like. A special form of topical administration is delivery by a transdermal patch. Methods for preparing transdermal patches are disclosed, e.g., in Brown, et al., *Annual Review of Medicine,* 39:221-229 (1988), which is incorporated herein by reference.

The active compounds can also be delivered by subcutaneous implantation for sustained release. This may be accomplished by using aseptic techniques to surgically implant the active compounds in any suitable formulation into the subcutaneous space of the anterior abdominal wall. Disulfiram implanted subcutaneously for sustained release has also been shown to be effective at an amount of 800 to 1600 mg to achieve a suitable plasma concentration. See, e.g., Wilson, et al., *J. Clin. Psych.* 45:242-247 (1984). Sustained release can be achieved by incorporating the active ingredients into a special carrier such as a hydrogel. Typically, a hydrogel is a network of high molecular weight biocompatible polymers, which can swell in water to form a gel like material. Hydrogels are generally known in the art. For example, hydrogels made of polyethylene glycols, or collagen, or 80% poly(glycolic-co-L-lactic acid) and 20% disulfiram are suitable. See, e.g., Phillips, et al., *J. Pharmaceut. Sci.* 73:1718-1720 (1984).

The active compounds can also be conjugated, i.e., covalently linked, to a water soluble non-immunogenic high molecular weight polymer to form a polymer conjugate. Advantageously, such polymers, e.g., polyethylene glycol, can impart solubility, stability, and reduced immunogenicity to the active compounds. As a result, the active compound in the conjugate when administered to a patient, can have a longer half-life in the body, and exhibit better efficacy. PEGylated proteins are currently being used in protein replacement therapies and for other therapeutic uses. For example, PEGylated adenosine deaminase (ADAGEN®) is being used to treat severe combined immunodeficiency disease (SCIDS). PEGylated L-asparaginase (ONCAPSPAR®) is being used to treat acute lymphoblastic leukemia (ALL). For a general review of PEG-protein conjugates with clinical efficacy. See, e.g., Burnham, *Am. J Hosp. Pharm.,* 15:210-218 (1994). Preferably, the covalent linkage between the polymer and the active compound is hydrolytically degradable and is susceptible to hydrolysis under physiological conditions. Such conjugates are known as "prodrugs" and the polymer in the conjugate can be readily cleaved off inside the body, releasing the free active compounds.

Alternatively, other forms controlled release or protection including microcapsules and nanocapsules generally known in the art, and hydrogels described above can all be utilized in oral, parenteral, topical, and subcutaneous administration of the active compounds.

Another preferable delivery form is using liposomes as carrier. Liposomes are micelles formed from various lipids such as cholesterol, phospholipids, fatty acids, and derivatives thereof. Active compounds can be enclosed within such micelles. Methods for preparing liposomal suspensions containing active ingredients therein are generally known in the art and are disclosed in, e.g., U.S. Pat. No. 4,522,811, which is incorporated herein by reference. Several anticancer drugs delivered in the form of liposomes are known in the art and are commercially available from Liposome Inc. of Princeton, N.J., U.S.A. It has been shown that liposomal can reduce the toxicity of the active compounds, and increase their stability.

The thiuram disulfide compound disulfiram can be effective when administered at an amount within the conventional clinical ranges determined in the art. Typically, it can be effective at an amount of from about 125 to about 1000 mg per day, preferably from about 250 to about 500 mg per day. However, the amount can vary with the body weight of the patient treated. The active ingredient may be administered at once, or may be divided into a number of smaller doses to be administered at predetermined intervals of time. The suitable dosage unit for each administration of disulfiram can be, e.g., from about 50 to about 1000 mg, preferably from about 250 to about 500 mg. The desirable peak plasma concentration of disulfiram generally is about 0.05 to about 10 µM, preferably about 0.5 to about 5 µM, in order to achieve a detectable therapeutic effect. However, a plasma concentration beyond such ranges may work as well.

The active compounds can also be administered in combination with other active agents that treats or prevents another disease or symptom in the patient treated. However, it is to be understood that such other active agents should not interfere with or adversely affect the effects of the active compounds of this invention on the cancer being treated. Such other active agents include but are not limited to antiviral agents, antibiotics, antifungal agents, anti-inflammation agents, antithrombotic agents, cardiovascular drugs, cholesterol lowering agents, hypertension drugs, and the like.

It is to be understood that cancer patients placed on disulfiram/metal ion therapy must be warned against exposure to alcohol in any form, to avoid the precipitation of nausea and vomiting from buildup of acetaldehyde in the bloodstream. Subjects therefore must not only refrain from ingesting alcohol containing beverages, but should also not ingest over the counter formulations such as cough syrups containing alcohol or even use rubbing alcohol topically.

One potential mechanism explaining the effect of disulfiram/metal ion is that disulfiram inhibits DNA binding of ATF/CREB in a manner facilitated by heavy metal ions. ATF/CREB transcription factors play prominent roles in cell proliferation and survival (Desdoutets, et al., *Mol. Cell Biol.* 15:3301-3309 (1995); Ahn, et al., *Mol. Cell Biol.* 18:967-977 (1998); Karuppayil, et al., *J. Biol. Chem.* 273:17303-17306 (1998); Narayan, et al., *J. Biol. Chem.* 271:18508-18513 (1996); Heiland, et al., *Eur. J. Biochem.* 217:813-822 (1993); Guo, et al., *Biochemistry* 36:14447-14455 (1997); Ruchand, et al., *Oncogene* 15:827-836 (1997); Huguier, et al., *Mol Cell Biol.* 18:7020-7029 (1998); and Andrisani, et al., *Crit. Rev. Eukaryotic Gene Expression* 9:19-32 (1999)), and others have suggested molecular disruption of ATF/CREB-mediated transcription for controlling melanoma growth (Jean, et al., supra; Ronai, et al., supra). However, other important cellular targets for disulfiram exist. Klatt, et al., supra; Mohr, et al., *J. Biol. Chem.* 274:9427-9430 (1999); Brennan, et al., *Biochem. J.* 320:975-981 (1996); Galter, et al., *Eur. J. Biochem.* 221:639-648 (1994); and Constantini, et al., *Oncogene* 19:307-314 (2000).

The in vivo mechanism of disulfiram is complex and involves conversion to active metabolites. Lipsky, et al., *Chem-Biol. Interactions* 130-132:93-102 (2001). The biologic effects of disulfiram are also diverse, and include effects other than transcriptions factor inhibition. Loo, et al., supra; Wang, et al., supra, Yakiach, et al., supra; Cen, et al., supra; Marikovsky, et al., supra; Nobel, et al., supra. Disulfiram is absorbed as its bis(diethyldithio-carbamato)copper(II) complex (Johansson, et al., Acta. *Psychitrica Scand, Suppl.* 369: 15-26 (1992)), suggesting that a heavy metal-thiolate chelate may be the active drug facilitating mixed disulfide formation with critical cysteines. Additional support for a thiolate-metal complex as the proximate effector is provided by results showing that the copper chelator bathocuprioine disulfonic acid reduces and media supplementation with copper(II) or other heavy metal ions facilitates melanoma growth inhibition by disulfiram, that the reducing agent dithiothreitol reverses growth inhibition from the thiolate diethyldithiocarbamate, and that X-ray crystallography confirms the structure of dithiocarbamate-metal ion complexes.

A growing literature points to cysteine mixed disulfide formation, followed by glutathione conjugation as a unique mechanism for regulating activity of cellular proteins. Nobel, et al., supra; Klatt, et al., supra; Mohr, et al., supra; Brennan, et al., supra; Galter, et al., supra; Constantini, et al., supra; and Davis, et al., *Biochemistry* 35:2482-2488 (1996). Also, mitochondrial membrane permeabilization and apoptosis are induced by thiol cross-linking reagents that modify cysteine 56 in the adenine nucleotide translocator of the permeability transition pore complex. Constantini, et al., supra. Studies suggesting that disulfiram induces melanoma apoptosis by redox-related superoxide ($O_2^-$) anion generation have employed as the $O_2^-$ detector dihydroethidium (Cen, et al., supra), which can be directly oxidized by cytochrome c (Benov, et al., *Free Rad. Biol. Med.* 25:826-831 (1998)) released from mitochrondrial permeablity transition pore opening. Thus, dithiocarbamate-metal ion complexes also promotes mitochrondia-mediated cell death. Currently cisplatin is the only approved metal-based chemotherapy. However, zinc and arsenic are anti-proliferative for tumors. Borovansky, et al., *Melanoma Res.* 7:449-453 (1997); Iguchi, et al., *Eur. J Biochem.* 253:766-770 (1998); and Soignet, et al., *N. Engl. J Med.* 339:1389-1391 (1998)) and zinc and other metals inhibit NF-κB and AP-1 (Connell, et al., *J. Am. Coll. Nutr.* 5:411-417 (1997); Shumilla, et al., *Archiv. Biochem. Biophys.* 349:346-362 (1998); Yang, et al., *FEBS Lett.* 361: 89-96 (1995); Handel, et al., *Proc. Natl. Acad. Sci. USA* 92:4496-4501 (1995). Therefore, dithiocarbamates are complexing agents for delivery of anti-proliferative metal ions to tumor cells.

Methods

Culture of Malignant Cells. Human malignant cell lines were obtained from American Type Tissue Culture Collection (Rockville, Md.). Melanoma cells lines CRL 1585 and 1619 were cultured in RPMI 1640 (GIBCO-BRL, Life Technologies, Grand Island, N.Y.) with 10% fetal bovine serum (FBS) and passed with nonenzymatic Cell Dissociation Solution (Sigma). The prostate adenocarcinoma cell line CRL 1435 (PC-3) was also cultured in RPMI 1640 with 10% FBS but passed with 0.05% trypsin and 0.53 mM ethylenediaminetetraacetic acid (EDTA). The squamous lung carcinoma NCI-H520 and the adenosquamous lung carcinoma NCI-H596 cell lines were grown in RPMI 1640 supplemented with 10% FBS, 10 mM N-2-hydroxyethylpiperazine-N'-2-ethanesulfonic acid (HEPES) and 1.0 mM sodium pyruvate and passed with trypsin/EDTA. The small cell lung carcinoma NCI-H82 was cultured as a suspension in RPMI 1640 with 10% FBS. All of the above were grown in a 37° C. humidified environment containing 5% $CO_2$/air. The breast carcinoma cell line MDA-MB-453 was grown in a 37° C. humidified environment with free atmospheric gas exchange, Leibovitz's L-15 medium with 2 mM L-glutamine and 10% FBS, and was passed with trypsin/EDTA.

Cell Treatments. Most of the experiments were performed with tetraethylthiuram disulfide, disulfiram (Sigma), which does not have a free thiol to act as an antioxidant. Malignant melanoma cells grown to confluence on 100×15 mm plastic Petri dishes were treated with 0-5 μM disulfiram plus 1.6 μM $CuSO_4$. Disulfiram is converted to its bis(diethyldithio-carbamato)copper(II) complex after passage through the acid environment of the stomach. Johansson, et al., supra. Therefore, Copper(II) was added along with disulfiram in some experiments to stimulate formation of the disulfiram-copper chelate form in which the drug is systemically absorbed. Disulfiram was dissolved in dimethylsulfoxide (DMSO) to a final concentration <0.3-0.5%. Equal volumes of DMSO were added to control experiments. Nuclear protein was harvested and electrophoretic mobility gel shift assays were performed as outlined below. To determine whether disulfiram and metal ions might directly influence transcription factor binding, 5 μM disulfiram and/or 1.6 μM $CuSO_4$ (final concentration) were added to the binding reaction of nuclear protein obtained from control cells stimulated with 10% FBS alone in the absence of drugs or metal ions. The binding reaction was then performed using either 2.5 mM dithiothreitol or 3.0 mM glutathione as the buffer reducing agent.

The effect of disulfiram (0.15 to 5.0 μM) or sodium diethyldithiocarbamate (1.0 μM) on proliferation of malignant cell lines was studied in cultures stimulated with 10% FBS. Cell numbers were quantitated 24-72 hours later as outlined below. In some experiments disulfiram was added immediately after cells were plated. In other experiments, cells were plated and allowed to grow for 24-72 hours before fresh media with disulfiram was added, and cell numbers were assayed 24-72 hr later. Synergy was studied between disulfiram and N,N'-bis(2-chloroethyl-N)-nitrosourea (carmustine 1.0 to 1,000 μM) or cisplatin (0.1 to 100 μg/ml) added to medium. The effect of metal ions on disulfiram was studied with 0.2 to 10 μM copper(II) (provided as $CuSO_4$), zinc(II) (as $ZnCl_2$), silver(I) (as silver lactate) or gold(III) (as $HAuCl_4 \cdot 3H_2O$) ions added to growth medium, buffered to physiologic pH. To provide a biologically relevant source of copper, medium was supplemented with human ceruloplasmin at doses replicating low and high normal adult serum concentrations (250 and 500 mg/ml).

The effect of disulfiram was studied on expression of CRE-regulated cell cycle proteins and proteins influencing apoptosis. Confluent cells treated with 5 μM disulfiram or 5 μM disulfiram plus 1.6 μM $CuSO_4$ for 2 to 48 hours. Cells were lysed and levels of the pro-apoptotic protein p53, the anti-apoptotic protein Bcl-2, the cyclin inhibitor $p21^{WAF1/CiP1}$, and the cyclins A and B1 were measured by immunoblots as described below.

Potential redox effects of disulfiram were studied in three sets of experiments. The importance of cellular glutathione in thiocarbamate toxicity was studied by measuring levels of intracellular glutathione after treatment with disulfiram. Confluent monolayers were treated with disulfiram (5 μM), with or without 1.6 PM $CuSO_4$, and cells were harvested 24 hours later for measurement of glutathione. To assess whether a pro-oxidant effect of disulfiram accounts for growth inhibition, the effect of the potent lipophilic antioxidant probucol (1.0 to 1,000 μM) on disulfiram's anti-proliferative effect was studied. Finally, generation of intracellular oxidants in response to disulfiram (0.625 to 5 μM), copper(II) (0.2 to 1.6 μM $CuSO_4$) or 1.25 μM disulfiram plus various concentrations of copper(II) was measured directly, as outlined below.

To explore the role of cyclooxygenase inhibition on tumor growth, cells were cultured with or without disulfiram in the presence or absence of the cyclooxygenase-1 and cyclooxygenase-2 inhibitors indomethacin (5 μg/ml) or sodium salicylate (1 mM). To probe whether disulfiram might be inducing growth retardation by altering NO production, proliferation was studied with and without disulfiram in the presence and absence of the nitric oxide synthase inhibitor Nω-nitro-L-arginine added to growth medium (100 μM).

Finally, a number of dithiocarbamate effects have been attributed to increasing the intracellular levels of copper ions. Nobel, et al., *J. Biol. Chem.,* supra; Verhaegh, et al., *Mol. Cell Biol.* 1997;17:5966-570629 (1997); Erl, et al., supra. To further probe the role of copper ions in mediating cytotoxicity from disulfiram, cells were cultured with or without addition of the impermeate $Cu^{2+}$ chelator bathocuprioinedisulfonic acid (100 μM) added to medium to sequester $Cu^{2+}$ in the extracellular compartment. Cells were also treated 12 hours with various concentration of disulfiram (0.625 to 5.0 μM) and intracellular copper levels were measured as outlined below.

Electrophoretic Mobility Shift Assays. Nuclear protein was isolated and DNA binding reactions were performed and quantitated using the consensus oligonucleotides described in Brar, et al., *Am. J. Physiol. Cell Physiol.* 282:C1212-1224 (2002) for the cyclic-AMP responsive element CRE, for NF-κB (p50), and for activator protein-1 (AP-1). These oligonucleotides are available from ProMega, Madison, Wis. Competition experiments were performed with 10× unlabeled wild-type oligonucleotide sequences for CRE or NF-κB. Supershift experiments were performed by incubating the binding reaction with 1 μg of supershifting antibody (Santa Cruz Biotechnology) prior to electrophoresis.

Measurement of Proliferation in Cell Cultures. Proliferation of cultured cells seeded into 24-well uncoated plastic plates (Costar) at 50,000 cells per well was quantitated as previously detailed (Brar, et al., *J. Biol. Chem.* 274:20017-20026 (1999)) using a calorimetric method based upon metabolic reduction of the soluble yellow tetrazolium dye 3-[4,5-dimethylthiazol]-2yl-2,5-diphenyl tetrazolium bromide (MTT) to its insoluble purple formazan by the action of mitochondrial succinyl dehydrogenase. This assay was confirmed by experiments in which cells were stained with Wright's modified Giemsa, counterstained with eosin and counted directly at a magnification of ×100 using a 1-mm² ocular grid.

Measurement of Apoptosis. Apoptosis was studied by terminal deoxynucleotidyl transferase (TdT) dependent 3'-OH fluorescein end-labeling of DNA fragments, using a Fluorescein-FragEL™ DNA fragmentation detection kit (Oncogene Research Products, Cambridge, Mass.), by fluorescent-labeled annexin V staining of phosphatidylserine translocated to the membrane surface, using the Annexin-V FLUOS staining kit (Roche Molecular Biochemical, Indianapolis, Ind.), and by visually assessing endonuclease dependent DNA fragmentation on ethidium bromide-stained agarose gels.

DNA Cell Cycle Measurements. To study the effect of disulfiram on the DNA cell cycle, confluent cells were treated with 10% FBS plus DMSO vehicle, FBS and DMSO vehicle plus 250 mg/ml ceruloplasmin as a source of copper(II), FBS plus 5 μM disulfiram or FBS plus 5 μM disulfiram and 250 mg/ml ceruloplasmin. After 24 hours, cells were trypsinized, washed twice in cold Dulbecco's phosphate buffered saline (DPBS) with 1 mM EDTA and 1% BSA, fixed 30 minutes in ice-cold 70% ethanol, and stained by incubation for 30 minutes at 37° C. in a 10 mg/ml solution of propidium iodide in DPBS and 1 mg/ml RNase A. DNA cell cycle measurements were made using a FACStar$^{PLUS}$ Flow Cytometer (Becton-Dickinson, San Jose, Calif.).

Immunoblots for Proteins. Immunoblots were performed and quantitated as described previously (Brar, et al., *J. Biol. Chem.,* supra) using primary rabbit polyclonal antibodies against human bcl-2, p53, p21$^{WAF1/Cip1}$, cyclin A and cyclin B1, and peroxidase-labeled donkey polyclonal anti-rabbit IgG (Santa Cruz).

Measurement of Intracellular Copper. Cells were cultured in 12-well plastic tissue culture plates at an initial plating density of 50,000 cells/well, grown to confluence and treated with disulfiram or DMSO vehicle as outlined above. Media was removed and cells were washed twice with DPBS. Cells were then scraped into 1.0 ml of 3N HCl/10.0% trichloroacetic acid and hydrolyzed at 70° C. for 16 hours. The hydrolysate was centrifuged at 600 grams for 10 minutes to remove debris and copper was measured in the supernatant using inductively coupled plasma emission spectroscopy (Model P30, Perkin Elmer, Norwalk, Conn.) at wavelengths of 325.754 and 224.700 nm. To minimize metal contamination, plasticware rather than glassware was used in these experiments, and double-distilled, deionized water was used for all aqueous media. Results are reported as ng copper/culture well.

Measurement of Intracellular Generation of Reactive Oxygen Species. Generation of reactive oxygen species in response to disulfiram with or without $CuSO_4$ was studied using 2',7'-dichlorofluorescin diacetate (Molecular Probes, Eugene, Oreg.) and a modification of methods previously reported (Ubezio, et al., *Free Rad. Biol. Med.* 16:590-516 (1994)). Cells were plated in 24 well plastic plates at 50,000 cells per well and grown to confluence. Media was aspirated from wells and replaced with 100 μl medium containing 10 μM dichlorofluorescin diacetate, and plates were incubated at 37° C. for 30 minutes. The dichlorofluorescin diacetate containing media was aspirated, cells were washed twice with media alone and 100 μl fresh media was added to wells. With the plate on the fluorescence micro-plate reader (HTS 7000) cells were stimulated with 25 μl of media containing 5× concentrations of disulfiram and/or $CuSO_4$ to provide final concentrations of 0-5.0 μM disulfiram and/or 0-1.6 μM $CuSO_4$, respectively. The relative concentration of dichlorofluroescein was measured immediately by monitoring fluorescence at 37° C. using an excitation wavelength of 485 nm and emission wavelength of 535 nm.

Measurement of Intracellular Glutathione. Disulfiram (5 μM), with or without 1.6 μM $CuSO_4$, was added to cells grown to confluence on 100×15 mm plastic dishes, and cells were harvested 24 hours later for measurement of glutathione using the 5,5'-dithiobis(2-nitrobenzoic acid)-glutathione reductase recycling assay. (Anderson, et al., *Methods Enzymol.* 113:548-555 (1985)).

Synthesis of Thiocarbamate-Metal Chelates. Synthesis of diethyldithiolato metal complexes is well known and was performed following established procedures in the literature (Burns, et al., *Adv. Inorg. Chem. Radiochem.* 23:211-280 (1980)). Typically, aqueous solutions of a metal salt, e.g., $CuCl_2$, and sodium or ammonium diethyldithiocarbamate are mixed and the desired complex separated by extraction into an organic phase such as dichloromethane. The stoichiometric ratio between metal salt and diethyldithiocarbamate salt can influence the final stoichiometry of the product. Identical complexes were synthesized starting with disulfiram rather than diethyldithiocarbamate. All diethyldithiocarbamato metal complexes were characterized by means of a single crystal X-ray diffraction and structures were reported in the Cambridge Crystallographic database. The silver(I) and zinc (II) diethyldithiocarbamate complexes were found to be polymeric.

Study of Anti-Tumor Activity of Disulfiram and Zinc Supplementation In Vivo. Adult female CB17-SCID mice (Harlan, Indianapolis, Ind.) were housed in a protected laminar flow facility with access to water and either a standard diet containing 87 ppm zinc or a zinc supplemented diet (Harlan) containing 1,000 ppm zinc(II) as zinc acetate. After acclimatization to the Vivarium, mice were injected subcutaneously in the right groin with $5\times10^6$ cells from a highly aggressive malignant melanoma obtained from a Carolinas Medical Center patient. The frozen tumor was passaged twice in SCID mice to adapt it to in vivo growth before use in these experiments. On the day of tumor injection all mice began daily administration of drug. Drug was administered in a total volume of 0.2 ml by gastric gavage via smooth Teflon-tipped needles inserted trans-orally into the stomach. Four groups were studied: Tumor Control (n=10; 0.2 ml olive oil daily; zinc diet of 87 ppm); Zinc-Supplemented Control (n=10; 0.2 ml olive oil daily; zinc diet of 1,000 ppm); Disulfiram (n=10; disulfiram 200 mg/kg/day in 0.2 ml olive oil; zinc diet of 87 ppm); and Zinc-Supplemented Diet+Disulfiram (n=10; disulfiram 200 mg/kg/day in 0.2 ml olive oil; zinc diet of 1,000 ppm). Mice were examined daily, the tumor was measured in two dimensions and the tumor volume was estimated using the formula for an elipse. When estimated tumor volume approached 500 mm$^3$ (a size just prior to when tumor begin to ulcerate and animals begin to suffer weight loss), all mice were euthanized. Tumors were excised, weighed, fixed in formalin, sectioned and stained with hematoxylin and eosin or immunostained for factor VIII. Slides were coded and examined by a blinded observer who identified vessels as deposits of red cells. For each slide, the number of vessels were counted in four different fields representative of the tumor. The average number of vessels per field was averaged per biopsy specimen and used to evaluate tumor vascularity.

Open Study of Disulfiram and Zinc Gluconate in Patients with Metastatic Malignant Melanoma. A phase I/II open study to assess the safety and possible anti-tumor efficacy of treatment with disulfiram and zinc gluconate in patients with stage IV metastatic melanoma. The open label study was done with approval from the Carolinas Medical Center Institutional Review Board, informed consent was obtained from all participating subjects, and data was collected prospectively. Patients were on no other treatment for melanoma during this time. All had histologically confirmed metastatic melanoma, one or more measurable metastases on examination or scan, pre-study survival estimated to be less than 4 months, ECOG performance status of 0 or 1, and no alcohol use. Positron emission spectroscopy (PET) and computed axial tomography (CT) scans of chest, abdomen and pelvis were obtained prior to treatment and every 3-6 months until progression. An initial magnetic resonance image (MRI) of the brain was obtained and found to be negative in each case. Laboratory studies (sodium, potassium, chloride, bicarbonate, glucose, blood urea nitrogen, creatinine, liver function studies, albumin, calcium, and complete blood count) were obtained initially and every 1-2 months. Side effects were recorded monthly and as applicable using the National Cancer Institute's Common Toxicity Criteria, Version 2.0. Patients began drug dosing at 250 mg disulfiram (Antabuse®, Wyeth-Ayerst) daily with the largest meal of the day. This was briefly increased to 500 mg daily over 2-4 weeks, but was changed back to 250 mg daily in each case to minimize drug side effects. Zinc gluconate [50 mg chelated elemental zinc (II), General Nutrition Center] was given 3 times daily but not concurrent with disulfiram administration. This heavy metal and its dose were chosen for previously demonstrated safety in humans as the preventative treatment for Wilson's Disease. Doses of each agent were those currently recommended for treatment of alcoholism and Wilson's disease, respectively.

Statistical Analysis. Data are expressed as mean values+ standard error. The minimum number of replicates for all measurements was four, unless indicated. Data were analyzed by one-way analysis of variance or repeated measures two-way analysis of variance for analysis of group, time, and group-time interactions. If significant interactions were found, Tukey's studentized range or Newman-Keuls post hoc multiple comparisons tests were applied to locate the sources of differences. Significance was assumed at $p<0.05$.

EXAMPLE 1

In this experiment it was shown that disulfiram inhibits melanoma proliferation in a metal-dependent fashion.

CRL 1619 melanoma cells stimulated with 10% fetal bovine serum (FBS) were plated at a density of 50,000 cells per well, and DMSO vehicle (5 µl per ml) or disulfiram (DS) was added to wells at the indicated concentrations. After 24, 48, 72 or 96 hours, proliferation was quantitated by assessing the cell number-dependent reduction of the soluble yellow tetrazolium dye 3-[4,5-dimethylthiazol]-2yl-2,5-diphenyl tetrazolium bromide (MTT) to its insoluble formazan, measured as the absorbance at 540 nm ($A_{540}$).

As shown in FIG. 1, growth inhibition was greater at lower rather than higher concentrations (41±2% after 96 hours at 0.5 µM but only 17±3% at 5 µM, $p<0.001$) tested, suggesting that a significant additional effect over time of higher concentrations of disulfiram may be pro-apoptotic caspase inhibition, counteracting growth reduction. Two-way analysis of variance shows $p<0.001$ for group, time and group-time interaction. *Analyzed by one-way analysis of variance at each time point, all disulfiram-treated groups were significantly different ($p<0.001$) than untreated or DMSO vehicle treated groups. +Analyzed by Tukey's studentized range test, cells treated with 0.5 µM disulfiram grew significantly slower ($p<0.05$) after 72 or 96 hours compared to cells treated with 2.5 or 5.0 µM disulfiram.

Within the same concentration ranges, disulfiram also inhibited growth of other types of malignant cells (% inhibition: CRL1585 melanoma, 100±0%; prostatic adenocarcinoma, 86±2%; squamous cell lung cancer, 78±3%; adenosquamous cell lung cancer, 50±4%; and breast carcinoma, 100±0%; all $p<0.001$). Disulfiram also augmented the antiproliferative effect of cisplatin or carmustine on melanoma cells (4+1% inhibition of growth at 24 hours with 100 ng/ml cisplatin alone vs 17±3% inhibition with cisplatin and 2.5 µM disulfiram, $p<0.05$; 46±7% stimulation of growth at 24 hours with 10 µM carmustine alone vs 75±6% inhibition of growth with carmustine and 0.6 µM disulfiram, $p<0.001$), suggesting reduced resistance to chemotherapy.

EXAMPLE 2

Because thiocarbamates chelate metals, growth inhibition was studied to determine if it was contingent on disulfiram's ability to complex with metal ions from growth medium. It was found that disulfiram increased intracellular copper in melanoma monolayers (ng copper per well: control=56±7; DMSO vehicle=52±4; 1.25 µM disulfiram=102±5; 2.5 µM disulfiram=160±17; 5.0 µM disulfiram=195±3; all $p<0.01$ vs control or vehicle). Adding the cell impermeate $Cu^{2+}$ chelator bathocuproine disulfonic acid (BCPS) to growth medium reversed growth inhibition (% growth inhibition at 48 hours: 73±1% with 1.25 µM disulfiram; 36±4% with disulfiram+50 µM BCPS; 17±3% with disulfiram+100 µM BCPS; $p<0.001$ vs disulfiram alone).

Conversely, as shown in FIG. 2, supplementation of growth medium with copper(II) or zinc(II) enhanced the antiproliferative activity of disulfiram. CRL1619 human melanoma cells stimulated with 10% fetal bovine serum (FBS) were plated at a density of 50,000 cells per well and treated with concentrations shown of DMSO vehicle (5 μl/ml) or disulfiram (DS, 0.625 μM) and concentrations shown of $CuSO_4$, $ZnCl_2$, or their metal ions plus DMSO or disulfiram. After another 24 hours proliferation was quantitated as in FIG. 1. Addition of even 0.2 μM $CuSO_4$ to medium converts 0.625 μM disulfiram from a 50% inhibitory ($IC_{50}$) concentration into a 100% inhibitory ($IC_{100}$) concentration of drug. *p<0.01 and +p<0.001 compared to no $CuSO_4$ or $ZnCl_2$.

It was also found that intrinsic biologic sources of copper ions enhance the effects of disulfiram. The copper transport protein ceruloplasmin has cupric ions (Percival, et al., *Am. J. Physiol.* 258:3140-3146 (1990)) that serve as a source of copper to enhance disulfiram (70±2% growth inhibition at 24 hours with 0.625 μM disulfiram; 0±0% growth inhibition with 250 mg/ml human ceruloplasmin; 100±0% growth inhibition with disulfiram+ceruloplasmin, p<0.001 vs disulfiram alone).

Disulfiram treatment of melanoma cells slightly reduces the number of cells in $G_0$-$G_1$ and increases the portion in S phase of the cell cycle. Ceruloplasmin greatly magnifies these effects and produces a cell cycle arrest in S phase. Thus, the anti-proliferative effect of disulfiram appears co-dependent upon copper (II). Unsynchronized CRL1619 melanoma cells were grown in the presence of a DMSO vehicle (FIG. 3A), 5 μM disulfiram (FIG. 3B), or 5 μM disulfiram plus 250 mg/ml ceruloplasmin as a source of copper(II) (FIG. 3C). Twenty-four hours later, cells were harvested and flow cytometric cell cycle analysis was performed. The proportion of nuclei in each phase of the cell cycle was determined with MODFIT DNA analysis software. FIG. 3C shows that disulfiram combined with copper(II) induces S-phase cell cycle arrest in CRL1619 melanoma cells and apoptosis, i.e., the combination of disulfiram and ceruloplasmin further increases the number of cells in S phase over disulfiram alone, prevents progression into the $G_2$-M cell cycle and induces apoptosis. Approximately 6% of cells are apoptotic, over two-thirds of cells are in S phase, and none are in $G_2$-M.

Treatments that increase intracellular $Cu^{2+}$ might be expected to enhance generation of reactive oxygen species. However, disulfiram did not deplete glutathione (228±18 in untreated cells; 254±7 in DMSO vehicle controls; 273±11 nmoles glutathione/μg cell protein for cells with 5 μM disulfiram), and the combination of 5.0 μM disulfiram and 1.6 μM $CuSO_4$ even increased glutathione (293±16 nmoles glutathione/μg cell protein; p<0.05 compared to untreated cells). Likewise, neither disulfiram (0.625 to 5 μM), $CuSO_4$ (0.2-1.6 μM) nor the combination of 1.25 μM disulfiram and 0.2 to 1.6 μM $CuSO_4$ caused oxidation of dichloroflurorescin. The baseline fluorescence of 1,431±23 units was not increased by any of the treatments. In addition, the antioxidant probucol did not prevent disulfiram from reducing melanoma proliferation.

Augmentation of intracellular copper might also increase levels of nitric oxide (NO*) through $Cu^{2+}$-mediated decomposition of nitrosothiols. Arnelle, et al., *Biol. and Chem.* 1:56-64 (1997); Gorren, et al., *Archiv. Biochem. Biophys.* 330:219-2238 (1996). NO* might, in turn, induce mitochondrial permeability transition and apoptosis (Hortelano, et al., *FEBS Lett.* 410:373-377 (1997). However, while the nitric oxide synthase inhibitor N-nitro-L-arginine alone slightly enhanced cellular growth, it did not eliminate the antiproliferative effect of disulfiram (data not shown). Thus, disulfiram does not affect cellular redox state.

NF-κB inhibition by thiocarbamates is associated with facilitation of intracellular zinc transport (Kim, et al., *Europ. J. Pharmacol.* 392:133-136 (2000)), and zinc supplementation increases the toxicity of thiocarbamates for vascular smooth muscle cells. Erl, et al., *Am. J. Physiol. Cell Physiol.* 278:C116-C1125 (2000). Zinc substantially enhanced the antiproliferative potential of disulfiram against melanoma cells (See FIG. 2).

EXAMPLE 3

Dithiocarbamates chelate with other metals, such as $Au^{3+}$, $Cu^{2+}$, $Zn^{2+}$, $Ag^{1+}$, $Ga^{3+}$ or $Fe^{3+}$ were synthesized. A critical issue in relation to the effects of dithiocarbamates is the availability of the thiolate anion to condense with protein sulfhydryls. To assess whether the thiolate anion was present, x-ray crystallography was performed on synthesized chelates. FIG. 4 shows an x-ray crystallographic structure of gold(III) diethyldithiocarbamate. The structure of zinc(II) diethyldithiocarbamate chelate is shown in the x-ray crystallographic structure of FIG. 9. The structures of copper (II), silver (I), iron (III) and gallium (III) were also confirmed.

Complexes were generated as outlined in Methods. A Nonius Kappa-CCD diffractometer was used to collect X-ray diffraction data. The crystal diffracted well and a data set was collected to 27.5° using Mo Kα radiation (λ=0.71073 Å). Least-squares refinement on the cell parameters reveled an orthorhombic unit cell with a=11.5167(5), b=7.2472(2), c=12.9350(7) Å, and a volume of 1079.6(1) $Å^3$. Examination of the systematic absences showed the space group to be Pnma (#62). The structure was solved by direct methods using SIR92 and revealed the crystal to be dichloro(diethylthiocarbamato)gold (III). The structure was confirmed by the successful solution and refinement of the 83 independent variables for the 893 reflections to R-factors of 3.3 and 3.2%, with an ESD of 1.499. The gold complex is a square planar coordination complex in which the Au and the four coordinated atoms sit on a mirror at x, 0.25, z. The organic ligand was found to be disordered with the diethylamine ligand occupying two sites related to each other through the mirror plane. This compound inhibited CRL1619 melanoma growth by 95.0+1.5% after exposure for 48 hours to a concentration as low as 150 nM.

Gold and silver salts also enhanced the antiproliferative activity of disulfiram (% growth inhibition: 45±5% with 0.15 μM disulfiram; 0±0% with 5 μM silver lactate alone; 71±7% with disulfiram+silver lactate, p<0.001; 0±0% with 5 μM gold tetrachloride alone; 99±1% with disulfiram+gold tetrachloride, p<0.001).

To confirm that the proximate reactive dithiocarbamate structure important for promoting cellular mixed disulfide formation is the thiolate anion generated from fully reduced dithiocarbamates by metals, the anti-proliferative activity of the thiolate sodium diethyldithiocarbamate alone or in the presence of a low concentration of dithiothreitol to promote formation of the fully reduced thioacid was compared. Sodium diethyldithiocarbamate alone (1 μM) decreased melanoma proliferation by 92±2% after 48 hours (p<0.001), but growth was inhibited by only 24±3% (p<0.001) with simultaneous addition of a concentration of dithiothreitol (100 μM), which does not affect proliferation of melanoma cells by itself (0±0%).

EXAMPLE 4

This example shows that disulfiram and metals inhibit ATF/CREB DNA binding and cyclin A expression. One critical location of cysteines is the DNA binding region of transcription factors, where sulfhydryls generally must remain reduced to insure effective transcription factor binding. Klatt, et al., supra. To determine if thiocarbamates might form mixed disulfides with these sulfhydryls, DNA binding of the cyclic AMP response element CRE was studied.

Melanomas exhibited prominent constitutive DNA binding activity for CRE that was significantly reduced by treatment of cells with disulfiram and copper (II). The results are shown in FIG. 5A wherein treatment of melanoma cells with disulfiram and copper (II) inhibits transcription factor binding to CRE. CRL1619 melanoma cells were grown to 80% confluence, nuclear protein was harvested and electrophoretic mobility gel shift assays (EMSAs) were performed using the consensus oligonucleotides described in Brar, et al., Am. J. Physiol. Cell Physiol., supra, for the cyclic-AMP responsive element CRE. Complex I is comprised of CREB-1 and ATF-1, and complex II contains ATF-2 (see online figure of supershift). The assays on the left show treatment of cultures for 6, 12 or 24 hours with the combination of 5 μM disulfiram and 1.6 μM cupric sulfate substantially interrupted transcription factor binding to CRE. The ATF-2 containing complex II proved the more sensitive to inhibition. EMSAs on the right side were performed using nuclear protein from replicate experiments (n=4) in which near confluent cells were treated for 8 hours and densitometry was performed on the ATF-2 containing upper complex II. The combination of disulfiram plus copper(II) reduced DNA binding by half. *p<0.05 compared to other treatments. Disulfiram and copper (II) also inhibited DNA binding of NF-κB and AP-1 (data not shown).

To determine if inhibition was from direct transcription factor modification, each agent was added to the binding reaction. The results are shown in FIG. 5B wherein the inhibitory effects of disulfiram or disulfiram plus copper(II) on transcription factor binding are potentiated in the presence of glutathione (GSH). EMSAs were performed with addition of disulfiram or disulfiram plus 1.6 μM CuSO$_4$ (Cu) directly to the binding reaction of nuclear protein and oligonucleotides. Disulfiram alone reduced DNA binding to CRE in the upper ATF-2 containing complex II (lane 3). This was magnified when disulfiram was combined with copper(II) ions (lane 5). Results are consistent with modest disruption of ATF-2 binding to CRE from formation of mixed disulfides between disulfiram and cysteines in the DNA binding region, and greater disruption when copper(II) is present to enhance mixed disulfide formation. However, reduction in CRE binding was much more pronounced when the binding reaction was performed with GSH instead of dithiothreitol (DTT) as the reducing agent [lane 7 for disulfiram, lane 9 for disulfiram plus copper(II)]. Inhibition of ATF-2 containing complex II binding to CRE by disulfiram and copper(II) in the presence of GSH was reversed by simultaneous addition of the potent uncharged reducing agent DTT (lane 10).

Copper (II) facilitated inhibition of CRE DNA binding by disulfiram (lane 5), suggesting that metal ions might enhance formation of a mixed disulfide between the thiuram disulfide and cysteine sulfhydryls in the transcription factor DNA binding region. Synergistic inhibition of transcription factor DNA binding by copper(II) and disulfiram was even more pronounced when dithiothreitol was replaced by glutathione as the reducing agent in the binding buffer (lane 9). This result suggests that glutathione, found in millimolar concentrations within the nucleus reacts with the mixed disulfide formed between the dithiocarbamate and protein cysteine sulfhydryls, leading to a bulky, negatively-charged glutathione-containing mixed disulfide that can more effectively disrupt DNA binding.

Disulfiram and copper(II) also reduced expression of cyclin A (FIG. 6), a phenomenon that would be expected to reduce cell cycle progression into G$_2$-M. Disulfiram had no consistent effect on expression of cyclin B1, p21$^{WAF1/CIP1}$, p53 or bcl-2. These results are shown in FIG. 6 wherein disulfiram and copper(II) reduce expression of the cell-cycle protein cyclin A. While disulfiram or copper(II) alone had little effect, treatment with the combination of disulfiram plus copper(II) reduced expression of cyclin A by over two-thirds at 24 hours, which would be expected to produce a site of cell cycle arrest consistent with that seen in FIG. 3. CRL1619 melanoma cells were plated at equal densities, grown to 80% confluence and in replicate experiments (n=4 each) treated with DMSO vehicle (lanes 1-4), 5 μM disulfiram (lanes 5-8), 1.6 μM CuSO$_4$ (Cu, lanes 9-12) or the combination of disulfiram and CuSO$_4$ (lanes 13-16). After 24 hours immunoblots were performed to assay for cyclin A. Quantitation of experiments by densitometry is shown below. Mean sum intensity of bands is displayed. *p<0.001 compared to all other treatments.

EXAMPLE 5

In this example disulfiram plus zinc supplementation decreased malignant melanoma growth in mice. To show this result melanoma cells were transplanted into SCID mice and grew rapidly as a spherical encapsulated mass. Adult female CB17-SCID mice (Harlan) were injected subcutaneously in the right groin with 5×10$^6$ cells from a highly aggressive malignant human melanoma. Mice were fed either a standard diet containing 87 ppm zinc or a zinc supplemented diet (Harlan) containing 1,000 ppm zinc(II) as zinc acetate. On the day of tumor injection all mice began daily oral gavage of 0.2 ml of olive oil as a control or 0.2 ml of olive oil containing the indicated drug. Four groups were studied: Tumor Control (Con; n=10; 0.2 ml olive oil daily; standard zinc diet of 87 ppm); Zinc-Supplemented Control (Zn; n=10; 0.2 ml olive oil daily; zinc diet of 1,000 ppm); Disulfiram (DS; n=10; disulfiram 200 mg/kg/day in 0.2 ml olive oil; zinc diet of 87 ppm); and Zinc-Supplemented Diet+Disulfiram (DS+Zn; n=10; disulfiram 200 mg/kg/day in 0.2 ml olive oil; zinc diet of 1,000 ppm). When estimated tumor volume in controls approached 500 mm$^3$, all mice were euthanized, and tumors were excised and weighed.

Histologic sections of tumors from mice treated with disulfiram plus zinc demonstrated more cellular necrosis. There was also a significant reduction in the number of blood vessels per field in disulfiram- or disulfiram plus zinc acetate-treated mice, suggesting that thiocarbamates inhibit angiogenesis (vessels per field=5.8±0.8 for control; 5.4±1.6 for zinc-supplemented; 2.5±0.7 for disulfiram, p<0.05 vs control; 2.0±0.7 for disulfiram+zinc, p<0.05 vs control). Mice in all groups tolerated treatment well, although diarrhea was noted in animals receiving disulfiram plus a zinc(II)-enriched diet. Tumor volume reached approximately 500 mm$^3$ in controls by 16 days, when animals were sacrificed.

The results are shown in FIG. 7 wherein disulfiram plus zinc supplementation decreases malignant melanoma growth in mice. Zinc(II) alone had no affect on tumor growth. However, treatment with disulfiram alone or disulfiram plus zinc (II) significantly inhibited tumor growth. $*p<0.05$ vs tumors in controls or Zn; $^+p<0.001$ vs tumors in controls or Zn. In mice receiving disulfiram and a zinc(II)-enriched diet, tumors were less than a third (83±12 mg) of the size of tumors in either controls (289±57 mg) or in mice receiving a zinc-enriched diet alone (271±19 mg).

EXAMPLE 6

Treatment of disulfiram and zinc(II) was given to humans and inhibited melanoma growth in patients. A phase I study of disulfiram and zinc gluconate in patients was conducted with advanced metastatic melanoma. The first three patients are presented:

Patient #1 was a 61 year old female who presented with a non-operable central liver metastasis from a T2 ocular melanoma that had been removed 5 years previously. The patient had developed abdominal pain and was found to have a 2.3 cm right hepatic metastasis and a 5.5 cm central liver metastasis confirmed as recurrent melanoma by biopsy. The patient declined chemotherapy or liver perfusion. Upon starting the protocol, the patient suffered grade 1 diarrhea, nausea, depression, and malaise. These side effects completely resolved within 2 months of continued treatment. The patient's abdominal pain also completely resolved and she returned to work. At 9 months, disulfiram was reduced to 250 mg per day. The patient continues on zinc gluconate 50 mg three times daily. All laboratory studies have remained normal. Repeated CT and PET scans at 3 months showed a >50% reduction in tumor size (FIG. 8). A PET scan 12 months after initiating treatment showed the lesions to be stable, and the patient remains clinically well after 17 months of therapy. FIG. 8 shows that disulfiram and zinc gluconate reduce hepatic tumor volume in a patient with metastatic ocular melanoma. Computed axial tomograms (top) and positron emission spectrographs (bottom) of patient #1 with Stage 1V ocular melanoma metastatic to the liver. Before treatment, the patient had a 5.5 cm central liver metastasis, shown in both scans by a white arrow. After 3 months of treatment with disulfiram 500 mg daily and zinc gluconate 50 mg three times daily, the hepatic metastasis had decreased in volume by >50% in both scans (arrows). After continuing treatment with 250 mg disulfiram daily and the same dose of zinc gluconate, the lesion remained stable in size at 10 and 14 months (arrows).

Patient #2 was a 44 year old woman who had a Clark level IV, 1.7 mm melanoma excised from her back 18 months prior to entering the study. This patient had a positive sentinel lymph node that was treated by axillary dissection. Initially, no additional metastases were found (Stage T3a, N1, M0). Patient #2 had received a year of adjuvant alpha interferon when routine PET and CT scans demonstrated diffuse metastatic disease. The patient was treated with high dose interleukin-2 without effect. Upon beginning the protocol, patient #2 had metastatic disease to mediastinal lymph nodes, liver, spleen and bones. Initially, patient #2 suffered grade 1 diarrhea and malaise. These side effects completely resolved within 2 months. Laboratory studies remained normal. When repeat CT and PET scans after 3 months of treatment showed progression at all sites, disulfiram and zinc gluconate were discontinued.

Patient #3 was a 57 year old woman who had a Clark Level III, 0.73 mm thick melanoma excised from her left back 9 years prior to entering the study. Patient #3 received no adjuvant treatment and developed a left axillary metastasis 4 years later, treated by axillary dissection. The patient received a year of adjuvant alpha interferon and 8 months later was found to have a chest wall and a lung metastasis. The patient was treated with high dose interleukin-2 but then developed additional axillary metastases requiring further dissection and radiation. Patient #3 refused standard chemotherapy. When beginning disulfiram and zinc gluconate, the patient had metastatic disease to the pelvic lymph nodes, left lung, and multiple subcutaneous sites. Initially, patient #3 suffered grade 1 diarrhea, fatigue, malaise, increased anxiety and depression. Diarrhea and malaise completely resolved within 2 months. Anxiety and depression were controlled with medication. Laboratory studies remained normal. Patient #3 temporarily stopped treatment for 5 weeks so that the patient could consume alcohol at a wedding, but resumed treatment at 250 mg disulfiram daily and 50 mg zinc gluconate three times daily and remained clinically stable and free of tumor progression 12 months after first initiating therapy. Interval PET scans showed no new lesions, 3 lung and lymph node mestastases that are stable, resolution of an area of soft tissue metastasis at the right iliac crest, and development of central necrosis in an area of soft tissue metastasis in the posterior left shoulder.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method for treating established cancer in a mammal, said cancer selected from the group consisting of melanoma, lung cancer, breast cancer, hepatic cancer, colorectal cancer, and prostatic carcinoma, and said method comprising administering to said mammal in need thereof a therapeutically effective amount of disulfiram and a therapeutically effective amount of a pharmaceutically suitable source of zinc ions.

2. The method of claim 1, wherein said pharmaceutically suitable source of zinc ions is administered as a complex with said disulfiram.

3. The method of claim 1, wherein said disulfiram and said pharmaceutically suitable source of zinc ions are administered separately.

4. The method of claim 1, wherein said disulfiram and said pharmaceutically suitable source of zinc ions are administered orally.

5. The method of claim 1, wherein said disulfiram and said pharmaceutically suitable source of zinc ions are administered intravenously.

6. The method of claim 1, wherein said disulfiram is administered at a dosage of from about 125 to about 1000 mg.

7. The method of claim 1, wherein said pharmaceutically suitable source of zinc ions is zinc acetate.

8. The method of claim 1, wherein said pharmaceutically suitable source of zinc ions is zinc gluconate.

9. The method of claim 1, wherein said pharmaceutically suitable source of zinc ions is zinc chloride.

10. The method of claim 1, wherein said cancer is melanoma.

11. The method of claim 1, wherein said cancer is hepatic cancer.

12. The method of claim 1, wherein said cancer is colorectal cancer.

13. The method of claim 1, wherein said cancer is prostatic carcinoma.

14. The method of claim 1, wherein said cancer is lung cancer.

15. The method of claim 1, wherein said cancer is breast cancer.

* * * * *